US008200321B2

(12) United States Patent (10) Patent No.: US 8,200,321 B2
McCombie et al. (45) Date of Patent: Jun. 12, 2012

(54) METHOD FOR MEASURING PATIENT POSTURE AND VITAL SIGNS

(75) Inventors: Devin McCombie, Solana Beach, CA (US); Marshal Dhillon, San Diego, CA (US); Matt Banet, Kihei, HI (US)

(73) Assignee: Sotera Wireless, Inc., San Diego, CA (US)

( * ) Notice: Subject to any disclaimer, the term of this patent is extended or adjusted under 35 U.S.C. 154(b) by 234 days.

(21) Appl. No.: 12/469,151

(22) Filed: May 20, 2009

(65) Prior Publication Data
US 2010/0298655 A1 Nov. 25, 2010

(51) Int. Cl.
*A61B 5/00* (2006.01)
(52) U.S. Cl. ........ 600/513; 600/301; 600/508; 600/509; 600/515; 600/518
(58) Field of Classification Search ........................ None
See application file for complete search history.

(56) References Cited

U.S. PATENT DOCUMENTS

| | | |
|---|---|---|
| 4,653,498 A | 3/1987 | New, Jr. et al. |
| 4,656,287 A | 4/1987 | Imaizumi et al. |
| 4,802,486 A | 2/1989 | Goodman et al. |
| 5,025,791 A | 6/1991 | Niwa |
| 5,482,036 A | 1/1996 | Diab et al. |
| 5,490,505 A | 2/1996 | Diab et al. |
| 5,524,637 A | 6/1996 | Erickson |
| 5,632,272 A | 5/1997 | Diab et al. |
| 5,685,299 A | 11/1997 | Diab et al. |
| 5,769,785 A | 6/1998 | Diab et al. |
| 5,800,349 A | 9/1998 | Isaacson et al. |
| 5,941,836 A | 8/1999 | Friedman |
| 5,964,701 A | 10/1999 | Asada et al. |
| 5,971,930 A | 10/1999 | Elghazzawi |
| 6,002,952 A | 12/1999 | Diab et al. |
| 6,018,673 A | 1/2000 | Chin et al. |
| 6,036,642 A | 3/2000 | Diab et al. |
| 6,041,783 A | 3/2000 | Gruenke |
| 6,081,735 A | 6/2000 | Diab et al. |

(Continued)

OTHER PUBLICATIONS

Otto, et al., "System Architecture of a Wireless Body Area Sensor Network for Ubiquitous Health Monitoring", Journal of Mobile Multimedia, 1(4):307-326 2006.

(Continued)

*Primary Examiner* — Carl H Layno
*Assistant Examiner* — Deborah Malamud
(74) *Attorney, Agent, or Firm* — Michael A. Whittaker; Acuity Law Group, P.C.

(57) ABSTRACT

The invention provides a system and method for measuring vital signs (e.g. SYS, DIA, SpO2, heart rate, and respiratory rate) and motion (e.g. activity level, posture, degree of motion, and arm height) from a patient. The system features: (i) first and second sensors configured to independently generate time-dependent waveforms indicative of one or more contractile properties of the patient's heart; and (ii) at least three motion-detecting sensors positioned on the forearm, upper arm, and a body location other than the forearm or upper arm of the patient. Each motion-detecting sensor generates at least one time-dependent motion waveform indicative of motion of the location on the patient's body to which it is affixed. A processing component, typically worn on the patient's body and featuring a microprocessor, receives the time-dependent waveforms generated by the different sensors and processes them to determine: (i) a pulse transit time calculated using a time difference between features in two separate time-dependent waveforms, (ii) a blood pressure value calculated from the time difference, and (iii) a motion parameter calculated from at least one motion waveform.

27 Claims, 14 Drawing Sheets

U.S. PATENT DOCUMENTS

| | | | |
|---|---|---|---|
| 6,094,592 | A | 7/2000 | Yorkey et al. |
| 6,129,686 | A | 10/2000 | Friedman |
| 6,157,850 | A | 12/2000 | Diab et al. |
| 6,160,478 | A | 12/2000 | Jacobsen et al. |
| 6,199,550 | B1 | 3/2001 | Wiesmann et al. |
| 6,261,247 | B1 | 7/2001 | Ishikawa et al. |
| 6,263,222 | B1 | 7/2001 | Diab et al. |
| 6,334,065 | B1 | 12/2001 | Al-Ali et al. |
| 6,491,647 | B1 | 12/2002 | Bridger et al. |
| 6,527,729 | B1 | 3/2003 | Turcott |
| 6,551,252 | B2 | 4/2003 | Sackner et al. |
| 6,584,336 | B1 | 6/2003 | Ali et al. |
| 6,605,038 | B1 | 8/2003 | Teller et al. |
| 6,606,993 | B1 | 8/2003 | Wiesmann et al. |
| 6,650,917 | B2 | 11/2003 | Diab et al. |
| 6,699,194 | B1 | 3/2004 | Diab et al. |
| 6,745,060 | B2 | 6/2004 | Diab et al. |
| 6,770,028 | B1 | 8/2004 | Ali et al. |
| 6,845,256 | B2 | 1/2005 | Chin et al. |
| 6,879,850 | B2 | 4/2005 | Kimball |
| 6,934,571 | B2 | 8/2005 | Wiesmann et al. |
| 6,947,781 | B2 | 9/2005 | Asada et al. |
| 7,020,508 | B2 | 3/2006 | Stivoric et al. |
| 7,020,578 | B2 | 3/2006 | Sorensen et al. |
| 7,041,060 | B2 | 5/2006 | Flaherty et al. |
| 7,194,293 | B2 | 3/2007 | Baker, Jr. |
| 7,215,984 | B2 | 5/2007 | Diab et al. |
| 7,257,438 | B2 | 8/2007 | Kinast |
| 7,299,159 | B2 | 11/2007 | Nanikashvili |
| 7,301,451 | B2 | 11/2007 | Hastings |
| 7,314,415 | B2 | 1/2008 | Umemura |
| 7,420,472 | B2 | 9/2008 | Tran |
| 7,455,643 | B1 | 11/2008 | Li et al. |
| 7,468,036 | B1 | 12/2008 | Rulkov et al. |
| 7,477,143 | B2 | 1/2009 | Albert |
| 7,485,095 | B2 | 2/2009 | Shusterman |
| 7,502,643 | B2 | 3/2009 | Farringdon et al. |
| 7,508,307 | B2 | 3/2009 | Albert |
| 7,522,035 | B2 | 4/2009 | Albert |
| 7,539,532 | B2 | 5/2009 | Tran |
| 7,541,939 | B2 | 6/2009 | Zadesky et al. |
| 7,586,418 | B2 | 9/2009 | Cuddihy et al. |
| 7,598,878 | B2 | 10/2009 | Goldreich |
| 7,602,301 | B1 | 10/2009 | Stirling et al. |
| 7,616,110 | B2 | 11/2009 | Crump et al. |
| 7,625,344 | B1 | 12/2009 | Brady et al. |
| 7,628,071 | B2 | 12/2009 | Sasaki et al. |
| 7,628,730 | B1 | 12/2009 | Watterson et al. |
| 7,641,614 | B2 | 1/2010 | Asada et al. |
| 7,648,463 | B1 | 1/2010 | Elhag et al. |
| 7,670,295 | B2 | 3/2010 | Sackner et al. |
| 7,674,230 | B2 | 3/2010 | Reisfeld |
| 7,678,061 | B2 | 3/2010 | Lee et al. |
| 7,684,954 | B2 | 3/2010 | Shahabdeen et al. |
| 7,689,437 | B1 | 3/2010 | Teller et al. |
| 7,698,101 | B2 | 4/2010 | Alten et al. |
| 7,698,830 | B2 | 4/2010 | Townsend et al. |
| 7,698,941 | B2 | 4/2010 | Sasaki et al. |
| 7,715,984 | B2 | 5/2010 | Ramakrishnan et al. |
| 2004/0133079 | A1 | 7/2004 | Mazar et al. |
| 2007/0055163 | A1 | 3/2007 | Asada et al. |
| 2007/0244376 | A1 | 10/2007 | Wang |
| 2008/0039731 | A1 | 2/2008 | McCombie et al. |
| 2008/0101160 | A1 | 5/2008 | Besson |

OTHER PUBLICATIONS

International Search Report and Written Opinion mailed Oct. 15, 2010 in PCT/US2010/035550.

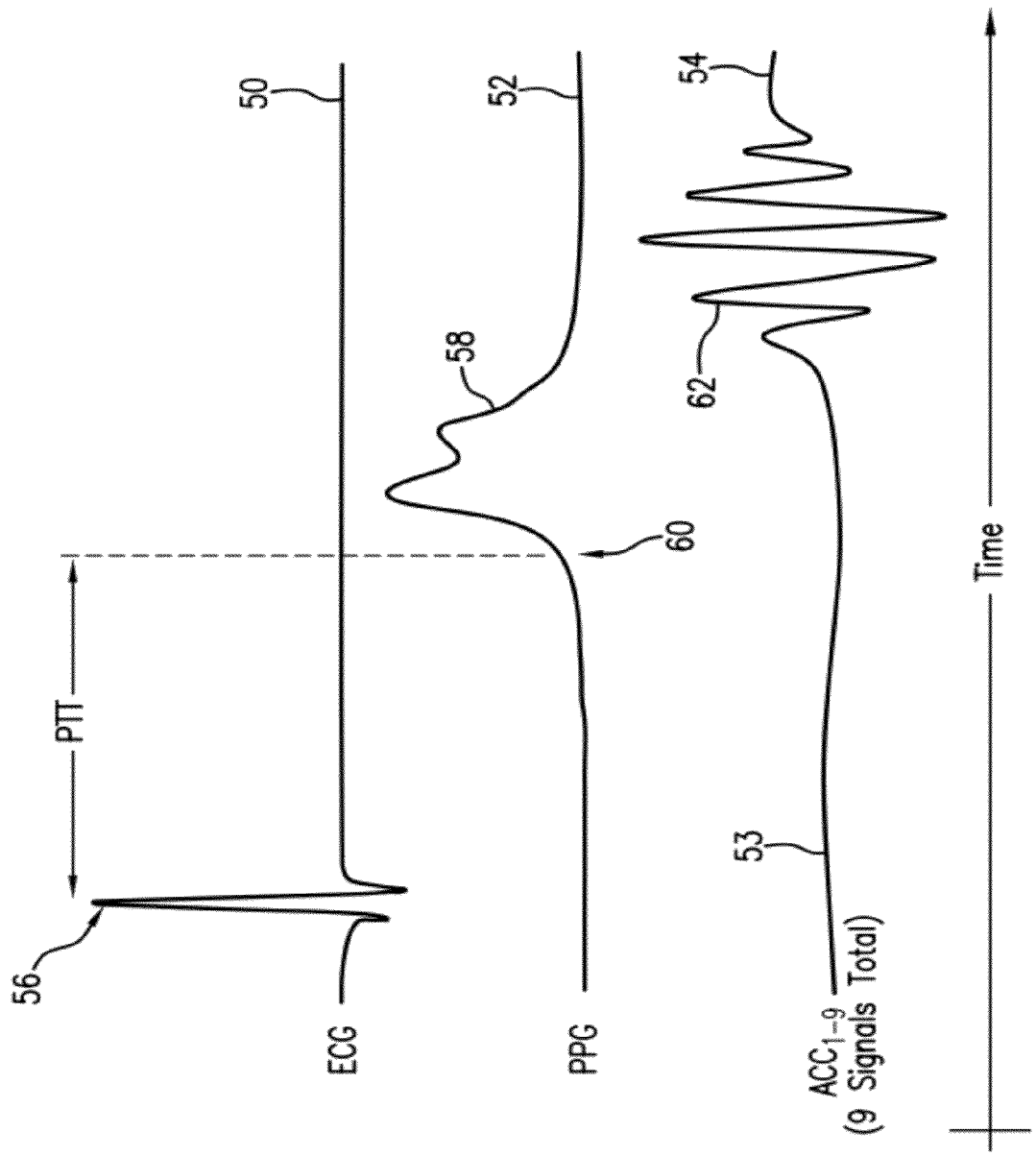

METHOD FOR MEASURING PATIENT POSTURE AND VITAL SIGNS

CROSS REFERENCES TO RELATED APPLICATION

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to medical devices for monitoring vital signs, e.g., arterial blood pressure.

2. Description of the Related Art

Pulse transit time (PTT), defined as the transit time for a pressure pulse launched by a heartbeat in a patient's arterial system, has been shown in a number of studies to correlate to systolic (SYS), diastolic (DIA), and mean (MAP) blood pressure. In these studies, PTT is typically measured with a conventional vital signs monitor that includes separate modules to determine both an electrocardiogram (ECG) and pulse oximetry (SpO2). During a PTT measurement, multiple electrodes typically attach to a patient's chest to determine a time-dependent ECG component characterized by a sharp spike called the 'QRS complex'. The QRS complex indicates an initial depolarization of ventricles within the heart and, informally, marks the beginning of the heartbeat and a pressure pulse that follows. SpO2 is typically measured with a bandage or clothespin-shaped sensor that attaches to a patient's finger, and includes optical systems operating in both the red and infrared spectral regions. A photodetector measures radiation emitted from the optical systems that transmits through the patient's finger. Other body sites, e.g., the ear, forehead, and nose, can also be used in place of the finger. During a measurement, a microprocessor analyses both red and infrared radiation detected by the photodetector to determine the patient's blood oxygen saturation level and a time-dependent waveform called a photoplethysmograph ('PPG'). Time-dependent features of the PPG indicate both pulse rate and a volumetric absorbance change in an underlying artery caused by the propagating pressure pulse.

Typical PTT measurements determine the time separating a maximum point on the QRS complex (indicating the peak of ventricular depolarization) and a foot of the optical waveform (indicating the beginning the pressure pulse). PTT depends primarily on arterial compliance, the propagation distance of the pressure pulse (which is closely approximated by the patient's arm length), and blood pressure. To account for patient-dependent properties, such as arterial compliance, PTT-based measurements of blood pressure are typically 'calibrated' using a conventional blood pressure cuff. Typically during the calibration process the blood pressure cuff is applied to the patient, used to make one or more blood pressure measurements, and then left on the patient. Going forward, the calibration blood pressure measurements are used, along with a change in PTT, to determine the patient's blood pressure and blood pressure variability. PTT typically relates inversely to blood pressure, i.e., a decrease in PTT indicates an increase in blood pressure.

The PPG, like most signals detected with optical means, is strongly affected by motion of the patient. For example, if the pulse oximeter is placed on the patient's finger, then motion of the finger can influence both the blood flow and degree of ambient light detected by the oximeter's optical system. This, in turn, can add unwanted noise to the PPG.

A number of issued U.S. patents describe the relationship between PTT and blood pressure. For example, U.S. Pat. Nos. 5,316,008; 5,857,975; 5,865,755; and 5,649,543 each describe an apparatus that includes conventional sensors that measure an ECG and PPG, which are then processed to determine PTT. U.S. Pat. No. 5,964,701 describes a finger-ring sensor that includes an optical system for detecting a PPG, and an accelerometer for detecting motion.

SUMMARY OF THE INVENTION

This invention provides a body-worn vital sign monitor featuring a series of sensors that measure time-dependent PPG, ECG, motion (ACC), and pressure waveforms to continuously monitor a patient's vital signs, degree of motion, posture and activity level. Blood pressure, a vital sign that is particularly useful for characterizing a patient's condition, is typically calculated from a PTT value determined from the PPG and ECG waveforms. Once determined, blood pressure and other vital signs can be further processed, typically with a server within a hospital, to alert a medical professional if the patient begins to decompensate. Processing the combination of the patient's motion and vital sign information is particularly useful, as these components are integrally related: a patient that is walking, for example, may have an accelerated heart rate and is likely breathing; the system can thus be designed to not alarm on these parameters, even if they exceed predetermined, preprogrammed levels.

In one aspect, the above-described systems provide a body-worn vital sign monitor that features an optical sensor, typically worn on the patient's finger, which includes a light source that emits radiation and a photodetector that detects radiation after it irradiates a portion of the patient's body to generate a time-dependent PPG. The monitor also includes an electrical sensor featuring at least two electrodes that measure electrical signals from the patient's body, and an electrical circuit that receives the electrical signals and processes them to determine a time-dependent ECG. To determine the patient's motion, posture, and activity level, the monitor features at least three motion-detecting sensors, each configured to be worn on a different location on the patient's body and to generate at least one time-dependent ACC waveform. The electrical sensor and the three motion-detecting sensors are typically included in a cable system worn on the patient's arm. A processing component within the monitor connects to cable system to receive the ECG, PPG, and the at least one ACC waveform generated by each motion-detecting sensor. The processing component operates a first algorithm that processes the PPG and ECG to determine a time difference between a time-dependent feature in each waveform; a second algorithm that processes the time difference to determine a blood pressure value; and a third algorithm that collectively processes the ACC waveforms generated by each motion-detecting sensor to determine at least one 'motion parameter' (e.g. the patient's posture, activity level, arm height, and degree of motion). A wireless system within the monitor transmits the patient's blood pressure value and the motion parameter to a remote receiver.

In other embodiments, PTT can be calculated from time-dependent waveforms other than the ECG and PPG, and then processed to determine blood pressure. In general, PTT can be calculated by measuring a temporal separation between features in two or more time-dependent waveforms measured from the human body. For example, PTT can be calculated from two separate PPGs measured by different optical sensors disposed on the patient's fingers, wrist, arm, chest, or virtually any other location where an optical signal can be measured using a transmission or reflection-mode optical configuration. In other embodiments, PTT can be calculated using at least one time-dependent waveform measured with an acoustic sensor, typically disposed on the patient's chest. Or it can be calculated using at least one time-dependent waveform measured using a pressure sensor, typically disposed on the patient's bicep, wrist, or finger. The pressure sensor can include, for example, a pressure transducer, piezoelectric sensor, actuator, polymer material, or inflatable cuff.

In one aspect, the invention provides a system and method for measuring vital signs (e.g. SYS, DIA, SpO2, heart rate, and respiratory rate) and motion (e.g. activity level, posture, degree of motion, and arm height) from a patient. The system features: (i) first and second sensors configured to independently generate time-dependent waveforms indicative of one or more contractile properties of the patient's heart; and (ii) at least three motion-detecting sensors positioned on the forearm, upper arm, and a body location other than the forearm or upper arm of the patient. Each motion-detecting sensor generates at least one time-dependent motion waveform indicative of motion of the location on the patient's body to which it is affixed. A processing component, typically worn on the patient's body and featuring a microprocessor, receives the time-dependent waveforms generated by the different sensors and processes them to determine: (i) a pulse transit time calculated using a time difference between features in two separate time-dependent waveforms, (ii) a blood pressure value calculated from the time difference, and (iii) a motion parameter calculated from at least one motion waveform. A wireless communication system, also worn on the patient's body and connected to the processing component, transmits the blood pressure value and the motion parameter to a remote receiver.

The contractile property of the patient's heart, for example, can be a beat, expansion, contraction, or any time-dependent variation of the heart that launches both electrical signals and a bolus of blood in the patient. The time-dependent waveform that results from this process, for example, can be an ECG waveform measured from any vector on the patient, a PPG waveform, an acoustic waveform measured with a microphone, or a pressure waveform measured with a transducer. In general, these waveforms can be measured from any location on the patient.

In embodiments, the first sensor is an optical sensor featuring a source of electromagnetic radiation configured to irradiate tissue of the patient, and a detector configured to detect one or more properties of the electromagnetic radiation after it irradiates the tissue. This sensor can detect, for example, an optical waveform that is indicative of volumetric changes in the irradiated tissue caused by ventricular contraction of the patient's heart. More specifically, the optical waveform represents a time-dependent change in optical absorption of an underlying vessel resulting from the ejection of blood from the left ventricle. The second sensor can be a similar sensor, positioned on another portion of the patient's body, and configured to measure a similar, time-dependent waveform. In embodiments, the pulse transit time used to determine blood pressure is a time difference between a peak of a QRS complex of an ECG waveform and an inflection point in the optical waveform (corresponding, e.g., to a rising edge of the waveform). Alternatively, the transit time is determined from time-dependent features on two separate optical waveforms.

The remote receiver that receives information describing the patient's blood pressure values and motion is typically configured to generate an alarm condition based on the blood pressure value, wherein the alarm condition can be modified based on a motion parameter. For example, an alarm condition indicating a need for medical intervention can be modified (e.g., turned off) by a motion parameter indicating that the patient is ambulatory.

Typically each of the three motion-detecting sensors is an accelerometer. The motion-detecting sensor positioned on the forearm is typically worn on the wrist, proximate to the processing component. The motion-detecting sensor positioned on the upper arm is typically electrically connected to the processing component through a cable. And the third motion-detecting sensor is typically positioned on the chest, and is also electrically connected to the processing component through the same cable. When referring to the motion-detecting sensors, 'forearm', as used herein, means any portion of the arm below the elbow, e.g. the forearm, wrist, hand, and fingers. 'Upper arm' means any portion of the arm above and including the elbow, e.g. the bicep, shoulder, and armpit.

The motion waveform generated by the motion-detecting sensor on the upper arm is transmitted to the processing component through the cable as a first digital data stream. Similarly, the motion waveform generated by the motion-detecting sensor positioned at a body location other than the forearm or upper arm is transmitted to the processing component through the same cable as a second digital data stream, wherein the processing component can resolve the first and second digital data streams. One of the time-dependent waveforms is an ECG waveform that is transmitted to the processing component through the cable as a third digital data stream that is separately resolvable from each of the first and second digital data streams.

In embodiments, the cable features a terminal portion that includes: a connector configured for reversible attachment of one or more ECG electrodes; an ECG circuit that receives electrical signals from one or more ECG electrodes and process them to determine an ECG waveform; and an analog-to-digital converter that converts the ECG waveforms into the third digital data stream. The terminal portion can also include one of the motion-detecting sensors, and is typically positioned at a body location other than the forearm or upper arm of the patient. In embodiments, the terminal portion is attached to the patient's chest.

In another aspect, the invention features a cable system that measures physiologic signals and motion information from a patient. The cable system integrates with a first sensor configured to detect a first time-dependent physiological waveform indicative of one or more contractile properties of the patient's heart, and includes: (i) an electrical sensor featuring at least two electrodes connected to an electrical circuit that generates a time-dependent electrical waveform indicative of contractile properties of the patient's heart, and (ii) at least two motion-detecting sensors that each generate at least one time-dependent motion waveform. Both the cable and the first sensor connect to a processing component that performs functions similar to that described above. Collectively, these systems can measure a blood pressure based on PTT, as described above.

The cable features a transmission line connected to: (i) the electrical sensor configured to receive the time-dependent electrical waveform; and (ii) either one or two motion-detecting sensors configured to receive a time-dependent motion waveform. The motion-detecting sensors are typically worn on the patient's upper arm, lower arm, and chest, with these arm positions defined above. The cable additionally includes a terminal portion, similar to that described above, that features the electrical circuit that determines the time-dependent electrical waveform, at least one motion-detecting sensor that determines the time-dependent motion waveform, and at least one analog-to-digital converter that digitizes these two waveforms before they pass through the cable. As described above, these waveforms are digitized to form separate digital data streams that are separately resolvable by the processing component. The electrical circuit in the terminal portion connects to at least three electrodes, with each electrode configured to detect an electrical signal from the patient's body. The electrodes typically connect to single-wire cables that plug into the terminal portion, and are typically worn on the patient's chest in a conventional 'Einthoven's Triangle' configuration. In embodiments, the terminal portion is a removable component featuring an ECG circuit that, in its different configurations, supports three, five, and twelve-lead ECG systems.

In another aspect, the invention features a method for calibrating a PTT-based blood pressure measurement using changes in a patient's arm height. The system includes a first sensor (e.g. an optical sensor) that generates a first time-dependent waveform indicative of one or more contractile properties of the patient's heart; and an electrical sensor that generates a time-dependent electrical waveform indicative of one or more contractile properties of the patient's heart. At least two motion-detecting sensors positioned on separate locations on the patient's body (e.g. the upper and lower arms) generate time-dependent motion waveforms that can be processed to determine, e.g., arm height. A processing component, similar to that described above, processes the time-dependent waveforms to determine: (i) first and second arm positions calculated from one or more of the time-dependent motion waveforms; (ii) first and second time differences between features in the time-dependent waveforms acquired in, respectively, the first and second arm positions; (iii) first and second blood pressure values calculated, respectively, at the first and second arm positions; and (iv) a blood pressure factor calculated using the first blood pressure value and the first time difference, together with the second blood pressure value and the second time difference.

In embodiments, the processing component further features a display component that renders a graphic interface which instructs the patient to move their arm to the first arm position and then to the second arm position. The processing component can also include an audio component that provides comparable audible instructions. Alternatively, the processing component analyzes the time-dependent motion waveforms to automatically detect when the patient's arm is in the first and second positions. While in these positions it automatically determines the first and second time difference and the corresponding first and second blood pressure values, and finally uses this information to determine the blood pressure factor. Ideally information gathered from more than two arm positions is used to determine the blood pressure factor.

The blood pressure factor essentially represents a calibration for the PTT-based blood pressure measurement. Once it is determined, the processing component determines a third time difference from the two time-dependent waveforms, and determines a blood pressure value using this time difference and the blood pressure factor.

In embodiments, the system additionally includes a pneumatic system featuring an inflatable cuff, a pump, and a pressure sensor that, collectively, make an oscillometric blood pressure measurement. During a calibration measurement, the inflatable cuff attaches to the patient's arm and is inflated by the pump. The pressure sensor measures a time-dependent pressure waveform representing a pressure within the inflatable cuff. Pulsations in the patient's arm caused by their blood pressure are superimposed on the pressure waveform. This can be done while the cuff is inflating or deflating, with both these processes occurring at a rate of 7-10 mmHg to make an accurate blood pressure measurement. Once this measurement is complete, the processing component analyzes the time-dependent pressure waveform to calculate at least one cuff-based blood pressure value, which it then uses along with a time difference and the blood pressure factor to continuously determine the patient's blood pressure during future, cuff-free measurements.

In another aspect, the invention provides a method for monitoring a patient featuring the following steps: (i) detecting first and second time-dependent physiological waveform indicative of one or more contractile properties of the patient's heart with a first and second sensors configured to be worn on the patient's body; (ii) detecting sets of time-dependent motion waveforms with at least two motion-detecting sensors positioned on different locations on the patient's body; (iii) processing the first and second time-dependent physiological waveforms to determine at least one vital sign; (iv) analyzing at least a portion of each set of time-dependent motion waveforms, or a mathematical derivative thereof, to determine a motion parameter; (v) processing the motion parameter to determine a probability that the patient is undergoing a specific activity state; and (vi) estimating the patient's activity state based on the probability.

In embodiments, the method includes calculating a mathematical transform (e.g. a Fourier Transform) of at least one motion waveform to determine a frequency-dependent motion waveform (e.g. a power spectrum). The amplitude of at least one frequency component of the power spectrum can then be processed to determine the motion parameter. For example, a band of frequency components between 0-3 Hz typically indicates that the patient is walking, while a similar band between 0-10 Hz typically indicates that the patient is convulsing. A higher-frequency band between 0-15 Hz typically indicates that a patient is falling. In this last case, the time-dependent motion waveform typically includes a signature (e.g. a rapid change in value) that can be further processed to indicate falling. Typically this change represents at least a 50% change in the motion waveform's value within a time period of less than 2 seconds.

Additionally, the analysis can include measuring a time-dependent variation (e.g. a standard deviation or mathematical derivative) of least one motion waveform to determine the motion parameter. In other embodiments, the method includes determining the motion parameter by comparing a time-dependent motion waveform to a mathematical function using, e.g., a numerical fitting algorithm such as a linear least squares or Marquardt-Levenberg non-linear fitting algorithm.

In embodiments, the method further includes determining a logit variable' z, or a mathematical derivative thereof, wherein z is defined as:

$$z = b_0 + b_1 x_1 + b_2 x_2 + \ldots + b_m x_m$$

and wherein $b_0$, $b_1$, $b_2$, and $b_m$, are predetermined constants related to motion, and at least one of $x_0$, $x_1$, $x_2$, and $x_m$, is a motion parameter determined from an amplitude of at least one frequency component of the power spectrum or from a time-dependent waveform. The method then processes the logit variable z with a mathematical function to determine the probability that the patient is undergoing a specific activity state. For example, z can be processed to generate a probabil ity function P, or a mathematical derivative thereof, wherein P is defined as:

$$P = \frac{1}{1 - \exp(-z)}$$

and indicates a probability of an activity state. The method can then compare P, or a mathematical derivative thereof, to a predetermined threshold value to estimate the patient's activity state.

In embodiments this method is used to estimate activity and posture states such as resting, moving, sitting, standing, walking, running, falling, lying down, and convulsing. In embodiments, the vital sign determined with this method is blood pressure calculated from a time difference (e.g. a PTT value) between features in the ECG and PPG waveforms, or alternatively using features between any combination of time-dependent ECG, PPG, acoustic, or pressure waveforms. This includes, for example, two PPG waveforms measured from different locations on the patient's body.

In another aspect the invention provides a method for monitoring vital signs and posture of a patient. A monitor, similar to that described above, measures vital signs from time-dependent waveforms (e.g. any combination of optical, electrical, acoustic, or pressure waveforms) and a patient's posture with at least one motion-detecting sensor positioned on the patient's torso (e.g., an accelerometer positioned on the patient's chest). The processing component analyzes at least a portion of a set of time-dependent motion waveforms generated by the motion-detecting sensor to determine a vector corresponding to motion of the patient's torso. It then compares the vector to a coordinate space representative of how the motion-detecting sensor is oriented on the patient to determine a posture parameter (e.g. standing upright, sitting, and lying down).

To determine the vector the method includes an algorithm or computation function that analyzes three time-dependent motion waveforms, each corresponding to a unique axis of the motion-detecting sensor. The motion waveforms can yield three positional vectors that define a coordinate space. In a preferred embodiment, for example, the first positional vector corresponds to a vertical axis, a second positional vector corresponds to a horizontal axis, and the third positional vector corresponds to a normal axis extending normal from the patient's chest. Typically the posture parameter is an angle, e.g. an angle between the vector and at least one of the three positional vectors. For example, the angle can be between the vector and a vector corresponding to a vertical axis. The patient's posture is estimated to be upright if the angle is less than a threshold value that is substantially equivalent to 45 degrees (e.g., 45 degrees+/−10 degrees); otherwise, the patient's posture is estimated to be lying down. If the patient is lying down, the method can analyze the angle between the vector and a vector corresponding to a normal axis extending normal from the patient's chest. In this case, the patient's posture is estimated to be supine if the angle is less than a threshold value substantially equivalent to 35 degrees (e.g., 35 degrees+/−10 degrees), and prone if the angle is greater than a threshold value substantially equivalent to 135 degrees (e.g., 135 degrees+/−10 degrees). Finally, if the patient is lying down, the method can analyze the angle between the vector and a vector corresponding to a horizontal axis. In this case, the patient is estimated to be lying on a first side if the angle is less than a threshold value substantially equivalent to 90 degrees (e.g., 90 degrees+/−10 degrees), and lying on an opposing side if the angle is greater than a threshold value substantially equivalent to 90 degrees (e.g., 90 degrees+/−10 degrees).

Blood pressure is determined continuously and non-invasively using a technique, based on PTT, which does not require any source for external calibration. This technique, referred to herein as the 'composite technique', is carried out with a body-worn vital sign monitor that measures blood pressure and other vital signs, and wirelessly transmits them to a remote monitor. The composite technique is described in detail in the co-pending patent application entitled: VITAL SIGN MONITOR FOR MEASURING BLOOD PRESSURE USING OPTICAL, ELECTRICAL, AND PRESSURE WAVEFORMS (U.S. Ser. No. 12/138, 194; filed Jun. 12, 2008), the contents of which are fully incorporated herein by reference.

Still other embodiments are found in the following detailed description of the invention, and in the claims.

BRIEF DESCRIPTION OF THE DRAWINGS

FIG. 2 shows a graph of time-dependent waveforms (ECG, PPG, and $ACC_{1-9}$) generated by, respectively, the ECG system, the optical system, and the accelerometer system of FIG. 1;

DETAILED DESCRIPTION OF THE INVENTION

System Overview

Figure 1:
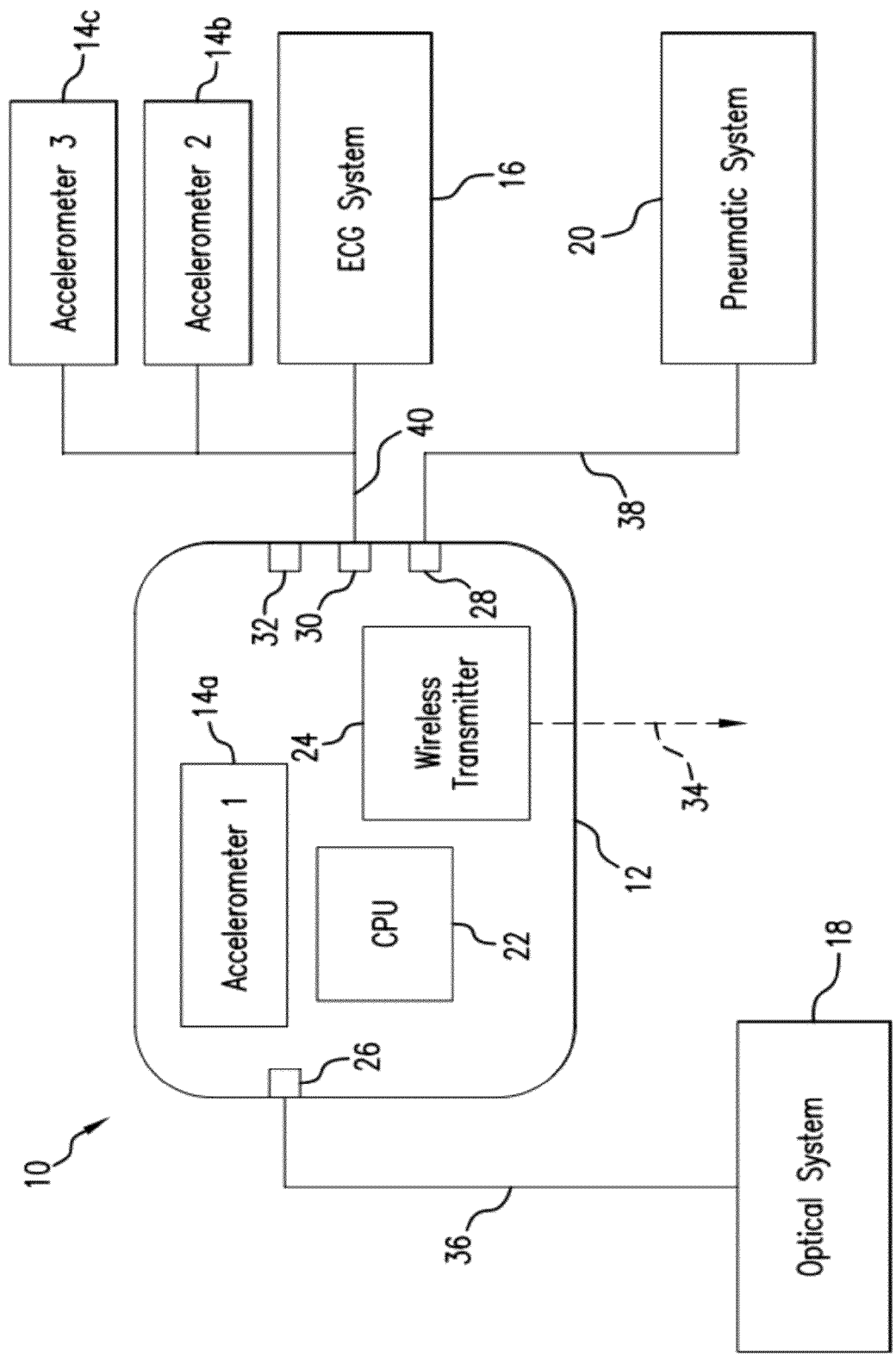
FIG. 1 shows a schematic drawing of a body-worn vital sign monitor featuring three accelerometers for detecting motion, along with ECG, optical, and pneumatic systems for measuring vital signs.

FIG. 1 shows a schematic drawing of a body-worn vital sign monitor 10 according to the invention featuring a wrist-worn transceiver 12 that continuously determines vital signs (e.g. SYS, DIA, SpO2, heart rate, respiratory rate, and temperature) and motion (e.g. posture, arm height, activity level, and degree of motion) for, e.g., an ambulatory patient in a hospital. The transceiver 12 connects to three separate accelerometers 14a, 14b, 14c distributed along a patient's arm and torso and connected to a single cable. Each of these sensors measures three unique ACC waveforms, each corresponding to a separate axis (x, y, or z), which are digitized internally and sent to a computer processing unit (CPU) 22 within the transceiver 12 for processing. The transceiver 12 also connects to an ECG system 16 that measures an ECG waveform, an optical system 18 that measures a PPG waveform, and a pneumatic system 20 for making cuff-based 'indexing' blood pressure measurements according to the composite technique. Collectively, these systems 14a-c, 16, 18, and 20 continuously measure the patient's vital signs and motion.

The ECG 16 and pneumatic 20 systems are stand-alone systems that include a separate microprocessor and analog-to-digital converter. During a measurement, they connect to the transceiver 12 through connectors 28, 30 and supply digital inputs using a communication protocol that runs on a controller-area network (CAN) bus. The CAN bus is a serial interface, typically used in the automotive industry, which allows different electronic systems to effectively communicate with each other, even in the presence of electrically noisy environments. A third connector 32 also supports the CAN bus and is used for ancillary medical devices (e.g. a glucometer) that is either worn by the patient or present in their hospital room.

The optical system 18 features an LED and photodetector and, unlike the ECG 16 and pneumatic 20 systems, generates an analog electrical signal that connects through a cable 36 and connector 26 to the transceiver 12. As is described in detail below, the optical 18 and ECG 16 systems generate synchronized time-dependent waveforms that are processed with the composite technique to determine a PTT-based blood pressure along with motion information. The body-worn vital sign monitor 10 measures these parameters continuously and non-invasively characterize the hospitalized patient.

The first accelerometer 14a is surface-mounted on a printed circuited board within the transceiver 12, which is typically worn on the patient's wrist like a watch. The second 14b accelerometer is typically disposed on the upper portion of the patient's arm and attaches to a cable 40 that connects the ECG system 16 to the transceiver 12. The third accelerometer 14c is typically worn on the patient's chest proximal to the ECG system 16. The second 14b and third 14c accelerometers integrate with the ECG system 16 into a single cable 40, as is described in more detail below, which extends from the patient's wrist to their chest and supplies digitized signals over the CAN bus. In total, the cable 40 connects to the ECG system 16, two accelerometers 14b, 14c, and at least three ECG electrodes (shown in FIGS. 3A and 3B, and described in more detail below). The cable typically includes 5 separate wires bundled together with a single protective cladding: the wires supply power and ground to the ECG system 16 and accelerometers 14b, 14c, provide high signal and low signal transmission lines for data transmitted over the CAN protocol, and provide a grounded electrical shield for each of these four wires. It is held in place by the ECG electrodes, which are typically disposable and feature an adhesive backing, and a series of bandaid-like disposable adhesive strips. This simplifies application of the system and reduces the number of sensing components attached to the patient.

To determine posture, arm height, activity level, and degree of motion, the transceiver's CPU 22 processes signals from each accelerometer 14a-c with a series of algorithms, described in detail below. In total, the CPU can process nine unique, time-dependent signals ($ACC_{1-9}$) corresponding to the three axes measured by the three separate accelerometers. Specifically, the algorithms determine parameters such as the patient's posture (e.g., sitting, standing, walking, resting, convulsing, falling), the degree of motion, the specific orientation of the patient's arm and how this affects vital signs (particularly blood pressure), and whether or not time-dependent signals measured by the ECG 16, optical 18, or pneumatic 20 systems are corrupted by motion. Once this is complete, the transceiver 12 uses an internal wireless transmitter 24 to send information in a series of packets, as indicated by arrow 34, to a central nursing station within a hospital. The wireless transmitter 24 typically operates on a protocol based on 802.11 and communicates with an existing network within the hospital. This information alerts a medical professional, such as a nurse or doctor, if the patient begins to decompensate. A server connected to the hospital network typically generates this alarm/alert once it receives the patient's vital signs, motion parameters, ECG, PPG, and ACC waveforms, and information describing their posture, and compares these parameters to preprogrammed threshold values. As described in detail below, this information, particularly vital signs and motion parameters, is closely coupled together. Alarm conditions corresponding to mobile and stationary patients are typically different, as motion can corrupt the accuracy of vital signs (e.g., by adding noise), and induce changes in them (e.g., through acceleration of the patient's heart and respiratory rates).

FIG. 2 shows time-dependent ECG 50, PPG 52, and $ACC_{1-9}$ 54 waveforms that the body-worn vital sign monitor continuously collects and analyzes to determine the patient's vital signs and motion. The ECG waveform 50, generated by the ECG system and three electrodes attached to the patient's chest, features a sharply peaked QRS complex 56. This complex 56 marks the peak of ventricular depolarization and informally indicates the beginning of each cardiac cycle. For a normal rhythm it occurs for each heartbeat. The optical system generates a PPG 52 using an infrared LED and matched photodetector incorporated into an optical sensor that attaches to the base of the patient's thumb. A pulsatile feature 58 in the PPG 52 follows the QRS complex 56, typically by about one to two hundred milliseconds, and indicates a volumetric expansion in arteries and capillaries disposed underneath the optical sensor. The temporal difference between the peak of the QRS complex 56 and the foot 60 of the pulsatile feature 58 in the PPG waveform is the PTT, which as described in detail below is used to determine blood pressure according to the composite technique.

Each accelerometer generates three time-dependent ACC waveforms 54 ($ACC_{1-9}$) that, collectively, indicate the patient's motion. Each waveform is digitized within the accelerometer using an internal analog-to-digital circuit. In general, the frequency and magnitude of change in the shape of the ACC waveform indicate the type of motion that the patient is undergoing. For example, a typical waveform 54 features a relatively time-invariant component 53 indicating a period of time when the patient is relatively still, and a time-variant component 62 when the patient's activity level increases. As described in detail below, a frequency-dependent analysis of these components yields the type and degree of patient motion. During operation, an algorithm running on the CPU within the wrist-worn transceiver operates an algorithm that performs this analysis so that the patient's activity level can be characterized in real time.

Figures 3A, 3B:
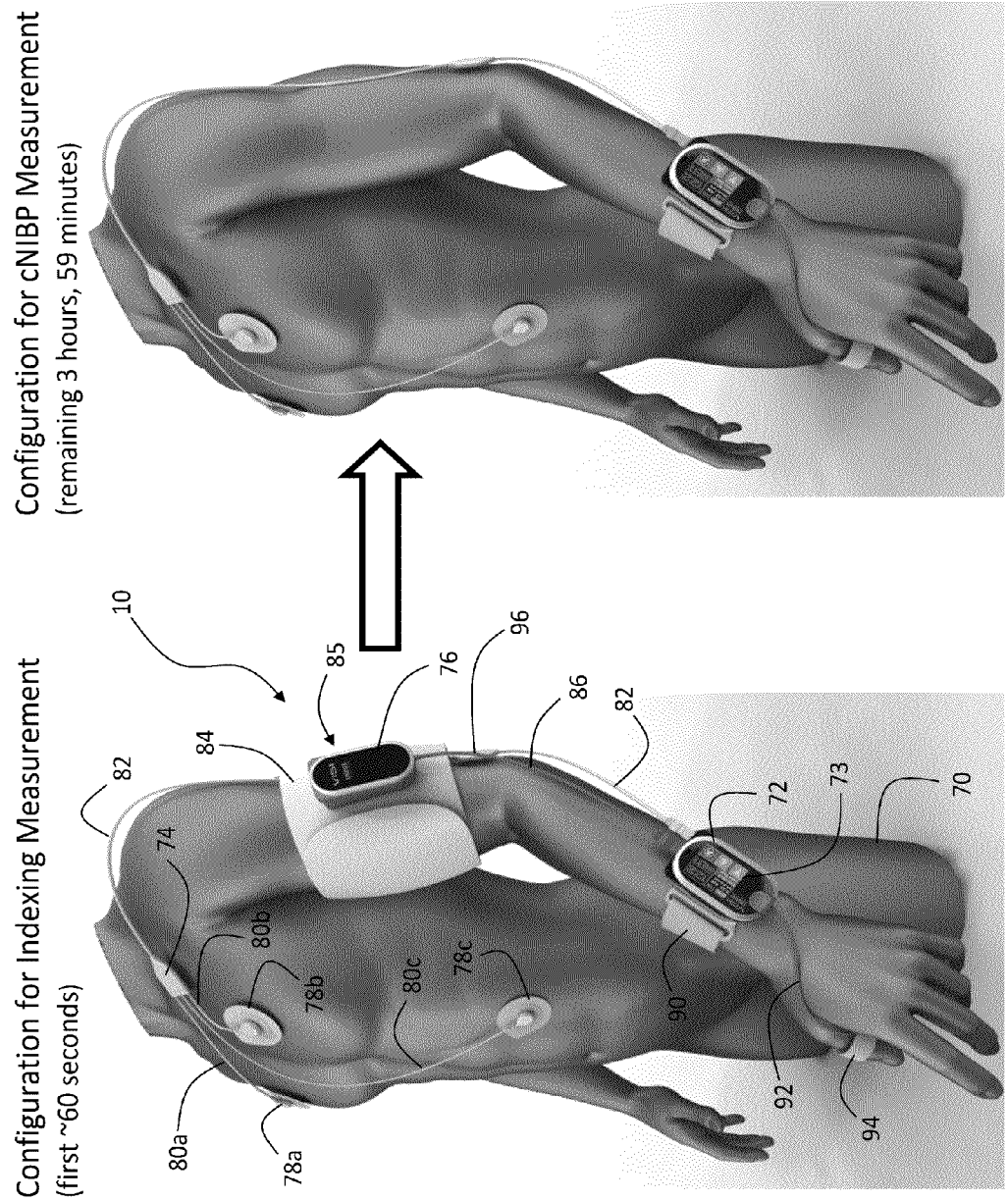
FIGS. 3A and 3B show an image of the body-worn vital sign monitor of FIG. 1 attached to a patient with and without, respectively, a cuff-based pneumatic system used for an indexing measurement.

FIGS. 3A and 3B show how the body-worn system 10 described with respect to FIG. 1 attaches to a patient 70. These figures show two configurations of the system: FIG. 3A shows the system used during the indexing portion of the composite technique, and includes a pneumatic, cuff-based system 85, while FIG. 3B shows the system used for subsequent continuous monitoring of the patient featuring a non-invasive blood pressure (cNIBP) measurement. The indexing measurement typically takes about 60 seconds, and is typically performed once every 4 hours. Once the indexing measurement is complete the cuff-based system is typically removed from the patient. The remainder of the time the system 10 performs the cNIBP measurement.

Figure 5:
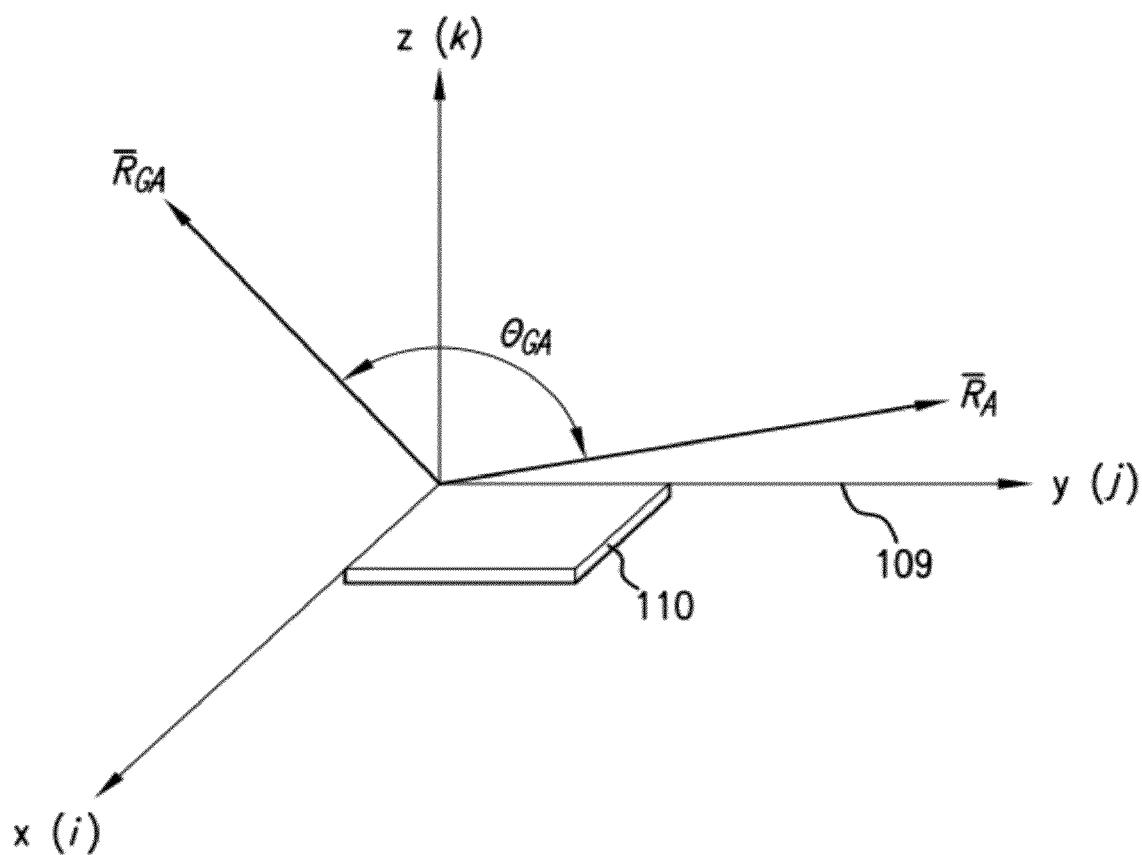
FIG. 5 shows a schematic drawing of a coordinate system used to calibrate accelerometers used in the body-worn vital sign monitor of FIGS. 3A and 3B.

The body-worn system 10 features a wrist-worn transceiver 72, described in more detail in FIG. 5, featuring a touch panel interface 73 that displays blood pressure values and other vital signs. A wrist strap 90 affixes the transceiver 72 to the patient's wrist like a conventional wristwatch. A cable 92 connects an optical sensor 94 that wraps around the base of the patient's thumb to the transceiver 72. During a measurement, the optical sensor 94 generates a time-dependent PPG, similar to the waveform 52 shown in FIG. 2, which is processed along with an ECG to measure blood pressure. PTT-based measurements made from the thumb yield excellent correlation to blood pressure measured with a femoral arterial line. As described in detail in the above-referenced patent application, this provides an accurate representation of blood pressure in the central regions of the patient's body.

To determine ACC waveforms, such as the time-dependent waveform 54 shown in FIG. 2, the body-worn vital sign monitor 10 features three separate accelerometers located at different portions on the patient's arm. The first accelerometer is surface-mounted on a circuit board in the wrist-worn transceiver 72 and measures signals associated with movement of the patient's wrist. The second accelerometer is included in a small bulkhead portion 96 included along the span of the cable 86. During a measurement, a small piece of disposable tape, similar in size to a conventional bandaid, affixes the bulkhead portion 96 to the patient's arm. In this way the bulkhead portion 96 serves two purposes: 1) it measures a time-dependent ACC waveform from the mid-portion of the patient's arm, thereby allowing their posture and arm height to be determined as described in detail below; and 2) it secures the cable 86 to the patient's arm to increase comfort and performance of the body-worn vital sign monitor 10.

The cuff-based module 85 features a pneumatic system 76 that includes a pump, valve, pressure fittings, pressure sensor, analog-to-digital converter, microcontroller, and rechargeable battery. During an indexing measurement, it inflates a disposable cuff 84 and performs two measurements according to the composite technique: 1) it performs an inflation-based measurement of oscillometry to determine values for SYS, DIA, and MAP; and 2) it determines a patient-specific relationship between PTT and MAP. These measurements are performed according to the composite technique, and are described in detail in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138, 194; filed Jun. 12, 2008), the contents of which have been previously incorporated herein by reference.

The cuff 84 within the cuff-based pneumatic system 85 is typically disposable and features an internal, airtight bladder that wraps around the patient's bicep to deliver a uniform pressure field. During the indexing measurement, pressure values are digitized by the internal analog-to-digital converter, and sent through a cable 86 according to the CAN protocol, along with SYS, DIA, and MAP blood pressures, to the wrist-worn transceiver 72 for processing as described above. Once the cuff-based measurement is complete, the cuff-based module 85 is removed from the patient's arm and the cable 86 is disconnected from the wrist-worn transceiver 72. cNIBP is then determined using PTT, as described in detail below.

To determine an ECG, similar to waveform 50 shown in FIG. 2, the body-worn vital sign monitor 10 features a small-scale, three-lead ECG circuit integrated directly into a bulkhead 74 that terminates an ECG cable 82. The ECG circuit features an integrated circuit that collects electrical signals from three chest-worn ECG electrodes 78a-c connected through cables 80a-c. The ECG electrodes 78a-c are typically disposed in a conventional 'Einthoven's Triangle' configuration which is a triangle-like orientation of the electrodes 78a-c on the patient's chest that features three unique ECG vectors. From these electrical signals the ECG circuit determines up to three ECG waveforms, which are digitized using an analog-to-digital converter mounted proximal to the ECG circuit, and sent through a cable 82 to the wrist-worn transceiver 72 according to the CAN protocol. There, the ECG is processed with the PPG to determine the patient's blood pressure. Heart rate and respiratory rate are determined directly from the ECG waveform using known algorithms, such as those described in the following reference, the contents of which are incorporated herein by reference: 'ECG Beat Detection Using Filter Banks', Afonso et al., IEEE Trans. Biomed Eng., 46:192-202 (1999). The cable bulkhead 74 also includes an accelerometer that measures motion associated with the patient's chest as described above.

There are several advantages of digitizing ECG and ACC waveforms prior to transmitting them through the cable 82. First, a single transmission line in the cable 82 can transmit multiple digital waveforms, each generated by different sensors. This includes multiple ECG waveforms (corresponding, e.g., to vectors associated with three, five, and twelve-lead ECG systems) from the ECG circuit mounted in the bulkhead 74, along with waveforms associated with the x, y, and z axes of accelerometers mounted in the bulkheads 75, 96. Limiting the transmission line to a single cable reduces the number of wires attached to the patient, thereby decreasing the weight and cable-related clutter of the body-worn monitor. Second, cable motion induced by an ambulatory patient can change the electrical properties (e.g. electrical impendence) of its internal wires. This, in turn, can add noise to an analog signal and ultimately the vital sign calculated from it. A digital signal, in contrast, is relatively immune to such motion-induced artifacts.

More sophisticated ECG circuits can plug into the wrist-worn transceiver to replace the three-lead system shown in FIGS. 3A and 3B. These ECG circuits can include, e.g., five and twelve leads.

Figure 4:
FIG. 4 shows an image of the wrist-worn transceiver featured in the body-worn vital sign monitor of FIGS. 3A and 3B.

FIG. 4 shows a close-up view of the wrist-worn transceiver 72. As described above, it attaches to the patient's wrist using a flexible strap 90 which threads through two D-ring openings in a plastic housing 106. The transceiver 72 features a touch-panel display 100 that renders a graphical user interface 73 which is altered depending on the viewer (typically the patient or a medical professional). Specifically, the transceiver 72 includes a small-scale infrared barcode scanner 102 that, during use, can scan a barcode worn on a badge of a medical professional. The barcode indicates to the transceiver's software that, for example, a nurse or doctor is viewing the user interface. In response, the user interface 73 displays vital sign data and other medical diagnostic information appropriate for medical professionals. Using this interface 73, the nurse or doctor, for example, can view the vital sign information, set alarm parameters, and enter information about the patient (e.g. their demographic information, medication, or medical condition). The nurse can press a button on the user interface 73 indicating that these operations are complete. At this point, the display 100 renders an interface that is more appropriate to the patient, e.g. it displays parameters similar to those from a conventional wristwatch, such as time of day and battery power.

As described above, the transceiver 72 features three CAN connectors 104a-c on the side of its upper portion, each which supports the CAN protocol and wiring schematics, and relays digitized data to the internal CPU. Digital signals that pass through the CAN connectors include a header that indicates the specific signal (e.g. ECG, ACC, or pressure waveform from the cuff-based module) and the sensor from which the signal originated. This allows the CPU to easily interpret signals that arrive through the CAN connectors 104a-c, and means that these connectors are not associated with a specific cable. Any cable connecting to the transceiver can be plugged into any connector 104a-c. As shown in FIG. 3A, the first connector 104a receives the cable 82 that transports a digitized ECG waveform determined from the ECG circuit and electrodes, and digitized ACC waveforms measured by accelerometers in the cable bulkhead 74 and the bulkhead portion 96 associated with the ECG cable 82.

The second CAN connector 104b shown in FIG. 4 receives the cable 86 that connects to the pneumatic cuff-based system 85 and used for the pressure-dependent indexing measurement. This connector is used to receive a time-dependent pressure waveform delivered by the pneumatic system 85 to the patient's arm, along with values for SYS, DIA, and MAP values determined during the indexing measurement. A user unplugs the cable 86 from the connector 104b once the indexing measurement is complete, and plugs it back in after approximately four hours for another indexing measurement.

The final CAN connector 104c can be used for an ancillary device, e.g. a glucometer, infusion pump, body-worn insulin pump, ventilator, or end-tidal $CO_2$ delivery system. As described above, digital information generated by these systems will include a header that indicates their origin so that the CPU can process them accordingly.

The transceiver includes a speaker 101 that allows a medical professional to communicate with the patient using a voice over Internet protocol (VOIP). For example, using the speaker 101 the medical professional could query the patient from a central nursing station or mobile phone connected to a wireless, Internet-based network within the hospital. Or the medical professional could wear a separate transceiver similar to the shown in FIG. 4, and use this as a communication device. In this application, the transceiver 72 worn by the patient functions much like a conventional cellular telephone or 'walkie talkie': it can be used for voice communications with the medical professional and can additionally relay information describing the patient's vital signs and motion.

Algorithms for Determining Patient Motion, Posture, Arm Height, Activity Level and the Effect of these Properties on Blood Pressure Described below is an algorithm for using the three accelerometers featured in the above-described body-worn vital sign monitor to calculate a patient's motion, posture, arm height, activity level. Each of these parameters affects both blood pressure and PTT, and thus inclusion of them in an algorithm can improve the accuracy of these measurements and the alarms and calibration procedures associated with them.

Calculating Arm Height

To calculate a patient's arm height it is necessary to build a mathematical model representing the geometric orientation of the patient's arm, as detected with signals from the three accelerometers. FIG. 5 shows a schematic image of a coordinate system 109 centered around a plane 110 used to build this model for determining patient motion and activity level, and arm height. Each of these parameters, as discussed in detail below, has an impact on the patient's vital signs, and particularly blood pressure.

The algorithm for estimating a patient's motion and activity level begins with a calculation to determine their arm height. This is done using signals from accelerometers attached to the patient's bicep (i.e., with reference to FIG. 3A, an accelerometer included in the bulkhead portion 96 of cable 86) and wrist (i.e. the accelerometer surface-mounted to the circuit board within the wrist-worn transceiver 72). The mathematical model used for this algorithm features a calibration procedure used to identify the alignment of an axis associated with a vector $R_A$, which extends along the patient's arm. Typically this is done by assuming the body-worn vital sign monitor is attached to the patient's arm in a consistent manner, i.e. that shown in FIGS. 3A and 3B, and by using preprogrammed constants stored in memory associated with the CPU. Alternatively this can be done by prompting the patient (using, e.g., the wrist-worn transceiver 72) to assume a known and consistent position with respect to gravity (e.g., hanging their arm down in a vertical configuration). The axis of their arm is determined by sampling a DC portion of time-dependent ACC waveforms along the x, y, and z axes associated with the two above-mentioned accelerometers (i.e. $ACC_{1-6}$; the resultant values have units of g's) during the calibration procedure, and storing these numerical values as a vector in memory accessible with the CPU within the wrist-worn transceiver.

The algorithm determines a gravitational vector $R_{GA}$ at a later time by again sampling DC portions of $ACC_{1-6}$. Once this is complete, the algorithm determines the angle $_{GA}$ between the fixed arm vector $R_A$ and the gravitational vector $R_{GA}$ by calculating a dot product of the two vectors. As the patient moves their arm, signals measured by the two accelerometers vary, and are analyzed to determine a change in the gravitational vector $R_{GA}$ and, subsequently, a change in the angle $_{GA}$. The angle $_{GA}$ can then be combined with an assumed, approximate length of the patient's arm (typically 0.8 m) to determine its height relative to a proximal joint, e.g. the elbow.

Figure 6:
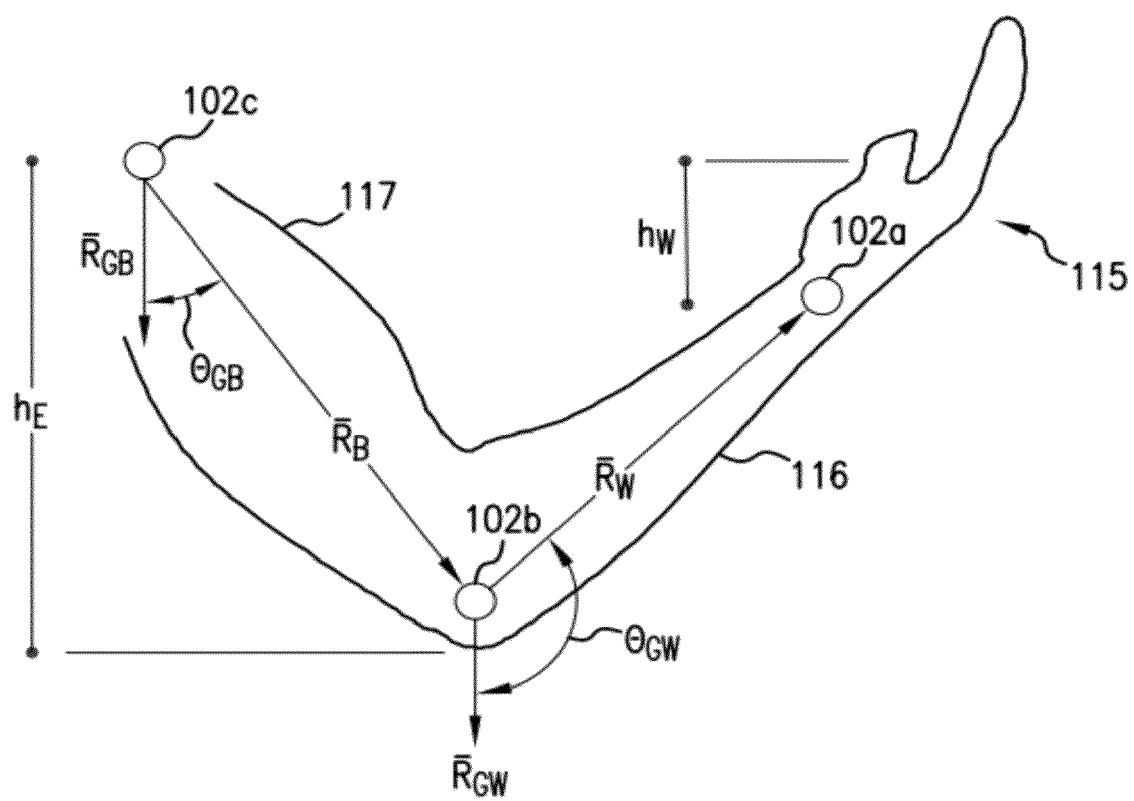
FIG. 6 shows a schematic drawing of the three accelerometers, attached to a patient's arm and connected to the body-worn vital sign monitor of FIGS. 3A, 3B, and 4.

FIG. 6 indicates how this model and approach can be extended to determine the relative heights of the upper 117 and lower 116 segments of a patient's arm 115. In this derivation, described below, i, j, k represent the vector directions of, respectively, the x, y, and z axes of the coordinate system 109 shown in FIG. 5. Three accelerometers 102a-c are disposed, respectively, on the patient's chest just above their armpit, near their bicep, and near their wrist; this is consistent with positioning within the body-worn vital sign monitor, as described in FIGS. 3A and 3B. The vector $R_B$ extending along the upper portion 117 of the patient's arm is defined in this coordinate system as:

$$\vec{R}_B = r_{Bx}\hat{i} + r_{By}\hat{j} + r_{Bz}\hat{k} \quad (1)$$

At any given time, the gravitational vector $R_{GB}$ is determined from ACC waveforms ($ACC_{1-3}$) using signals from the accelerometer 102b located near the patient's bicep, and is represented by equation (2) below:

$$\vec{R}_{GB}[n] = y_{Bx}[n]\hat{i} + y_{By}[n]\hat{j} + y_{Bz}[n]\hat{k} \quad (2)$$

Specifically, the CPU in the wrist-worn transceiver receives digitized signals representing the DC portion (e.g. component 53 in FIG. 2) of the $ACC_{1-3}$ signals measured with accelerometer 102b, as represented by equation (3) below, where the parameter n is the value (having units of g's) sampled directly from the DC portion of the ACC waveform:

$$y_{Bx}[n] = y_{DC,Bicep,x}[n]; y_{By}[n] = y_{DC,Bicep,y}[n]; y_{Bz}[n] = y_{DC,Bicep,z}[n] \quad (3)$$

The cosine of the angle $_{GB}$ separating the vector $R_B$ and the gravitational vector $R_{GB}$ is determined using equation (4):

$$\cos(\theta_{GB}[n]) = \frac{\vec{R}_{GB}[n] \cdot \vec{R}_B}{\|\vec{R}_{GB}[n]\| \|\vec{R}_B\|} \quad (4)$$

The definition of the dot product of the two vectors $R_B$ and $R_{GB}$ is:

$$\vec{R}_{GB}[n] \cdot \vec{R}_B = (y_{Bx}[n] \times r_{Bx}) + (y_{By}[n] \times r_{By}) + (y_{Bz}[n] \times r_{Bz}) \quad (5)$$

and the definitions of the norms or magnitude of the vectors $R_B$ and $R_{GB}$ are:

$$\|\vec{R}_{GB}[n]\| = \sqrt{(y_{Bx}[n])^2 + (y_{By}[n])^2 + (y_{Bz}[n])^2} \quad (6)$$

and $$\|\vec{R}_B\| = \sqrt{(r_{Bx})^2 + (r_{By})^2 + (r_{Bz})^2} \quad (7)$$

Using the norm values for these vectors and the angle $_{GB}$ separating them, as defined in equation (4), the height of the patient's elbow relative to their shoulder joint, as characterized by the accelerometer on their chest ($h_E$), is determined using equation (8), where the length of the upper arm is estimated as $L_B$:

$$h_E[n] = -L_B \times \cos(\theta_{GB}[n]) \quad (8)$$

As is described in more detail below, equation (8) estimates the height of the patient's arm relative to their heart. And this, in turn, can be used to further improve the accuracy of PTT-based blood pressure measurements.

The height of the patient's wrist joint $h_w$ is calculated in a similar manner using DC components from the time-domain waveforms ($ACC_{4-6}$) collected from the accelerometer 102a mounted within the wrist-worn transceiver. Specifically, the wrist vector $R_W$ is given by equation (9):

$$\vec{R}_W = r_{Wx}\hat{i} + r_{Wy}\hat{j} + r_{Wz}\hat{k} \quad (9)$$

and the corresponding gravitational vector $R_{GW}$ is given by equation (10):

$$\vec{R}_{GW}[n] = y_{Wx}[n]\hat{i} + y_{Wy}[n]\hat{j} + y_{Wz}[n]\hat{k} \quad (10)$$

The specific values used in equation (10) are measured directly from the accelerometer 102a; they are represented as n and have units of g's, as defined below:

$$y_{Wx}[n] = y_{DC,Wrist,x}[n]; y_{Wy}[n] = y_{DC,Wrist,y}[n]; y_{Wz}[n] = y_{DC,Wrist,z}[n] \quad (11)$$

The vectors $R_W$ and $R_{GW}$ described above are used to determine the cosine of the angle $_{GW}$ separating them using equation (12):

$$\cos(\theta_{GW}[n]) = \frac{\vec{R}_{GW}[n] \cdot \vec{R}_W}{\|\vec{R}_{WB}[n]\| \|\vec{R}_W\|} \quad (12)$$

The definition of the dot product between the vectors $R_W$ and $R_{GW}$ is:

$$\vec{R}_{GW}[n] \cdot \vec{R}_W = (y_{Wx}[n] \times r_{Wx}) + (y_{Wy}[n] \times r_{Wy}) + (y_{Wz}[n] \times r_{Wz}) \quad (13)$$

and the definitions of the norm or magnitude of both the vectors $R_W$ and $R_{GW}$ are:

$$\|\vec{R}_{GW}[n]\| = \sqrt{(y_{Wx}[n])^2 + (y_{Wy}[n])^2 + (y_{Wz}[n])^2} \quad (14)$$

and $$\|\vec{R}_W\| = \sqrt{(r_{Wx})^2 + (r_{Wy})^2 + (r_{Wz})^2} \quad (15)$$

The height of the patient's wrist $h_W$ can be calculated using the norm values described above in equations (14) and (15), the cosine value described in equation (12), and the height of the patient's elbow determined in equation (8):

$$h_W[n] = h_E[n] - L_W \times \cos(\theta_{GW}[n]) \quad (16)$$

In summary, the algorithm can use digitized signals from the accelerometers mounted on the patient's bicep and wrist, along with equations (8) and (16), to accurately determine the patient's arm height and position. As described below, these parameters can then be used to correct the PTT and provide a blood pressure calibration, similar to the cuff-based indexing measurement described above, that can further improve the accuracy of this measurement.

Calculating the Influence of Arm Height on Blood Pressure

A patient's blood pressure, as measured near the brachial artery, will vary with their arm height due to hydrostatic forces and gravity. This relationship between arm height and blood pressure enables two measurements: 1) a blood pressure 'correction factor', determined from slight changes in the patient's arm height, can be calculated and used to improve accuracy of the base blood pressure measurement; and 2) the relationship between PTT and blood pressure can be determined (like it is currently done using the indexing measurement) by measuring PTT at different arm heights, and calculating the change in PTT corresponding to the resultant change in height-dependent blood pressure. Specifically, using equations (8) and (16) above, and (21) below, an algorithm can calculate a change in a patient's blood pressure (BP) simply by using data from two accelerometers disposed on the wrist and bicep. The BP can be used as the correction factor. Exact blood pressure values can be estimated directly from arm height using an initial blood pressure value (determined, e.g., using the cuff-based module during an initial indexing measurement), the relative change in arm height, and the correction factor. This measurement can be performed, for example, when the patient is first admitted to the hospital. PTT determined at different arm heights provides multiple data points, each corresponding to a unique pair of blood pressure values determined as described above. The change in PTT values (PTT) corresponds to changes in arm height.

From these data, the algorithm can calculate for each patient how blood pressure changes with PTT, i.e. BP/PTT. This relationship relates to features of the patient's cardiovascular system, and will evolve over time due to changes, e.g., in the patient's arterial tone and vascular compliance. Accuracy of the body-worn vital sign monitor's blood pressure measurement can therefore be improved by periodically calculating BP/PTT. This is best done by: 1) combining a cuff-based initial indexing measurement to set baseline values for SYS, DIA, and MAP, and then determining BP/PTT as described above; and 2) continually calculating BP/PTT by using the patient's natural motion, or alternatively using well-defined motions (e.g., raising and lower the arm to specific positions) as prompted at specific times by monitor's user interface.

Going forward, the body-worn vital sign monitor measures PTT, and can use this value and the relationship determined from the above-described calibration to convert this to blood pressure. All future indexing measurements can be performed on command (e.g., using audio or visual instructions delivered by the wrist-worn transceiver) using changes in arm height, or as the patient naturally raises and lowers their arm as they move about the hospital.

To determine the relationship between PTT, arm height, and blood pressure, the algorithm running on the wrist-worn transceiver is derived from a standard linear model shown in equation (17):

$$PTT = \left(\frac{1}{m_{BP}}\right) \times P_{MAP} + \tilde{B} \quad (17)$$

Assuming a constant velocity of the arterial pulse along an arterial pathway (e.g., the pathway extending from the heart, through the arm, to the base of the thumb):

$$\frac{\partial (PWV)}{\partial r} = 0 \quad (18)$$

the linear PTT model described in equation (17) becomes:

$$\frac{\partial (PTT)}{\partial r} = \left(\frac{1}{L}\right)\left(\frac{1}{m_{BP}} \times MAP + \tilde{B}\right) \quad (19)$$

Equation (19) can be solved using piecewise integration along the upper 117 and lower 116 segments of the arm to yield the following equation for height-dependent PTT:

$$PTT = \quad (20)$$
$$\left(\frac{1}{m_{BP}} \times MAP + B\right) - \frac{1}{m_{BP}} \times \left[\left(\frac{L_1}{L}\right)\left(\frac{\rho G h_E}{2}\right) + \left(\frac{L_2}{L}\right)\left(\frac{\rho G}{2}(h_W + h_E)\right)\right]$$

From equation (20) it is possible to determine a relative pressure change $P_{rel}$ induced in a cNIBP measurement using the height of the patient's wrist ($h_W$) and elbow ($h_E$):

$$P_{rel}[n] = \left(\frac{L_1}{L}\right)\left(\frac{\rho G h_E[n]}{2}\right) + \left(\frac{L_2}{L}\right)\left(\frac{\rho G}{2}(h_W[n] + h_E[n])\right) \quad (21)$$

As described above, $P_{rel}$ can be used to both calibrate the cNIBP measurement deployed by the body-worn vital sign monitor, or supply a height-dependent correction factor that reduces or eliminates the effect of posture and arm height on a PTT-based blood pressure measurement.

Figure 10:
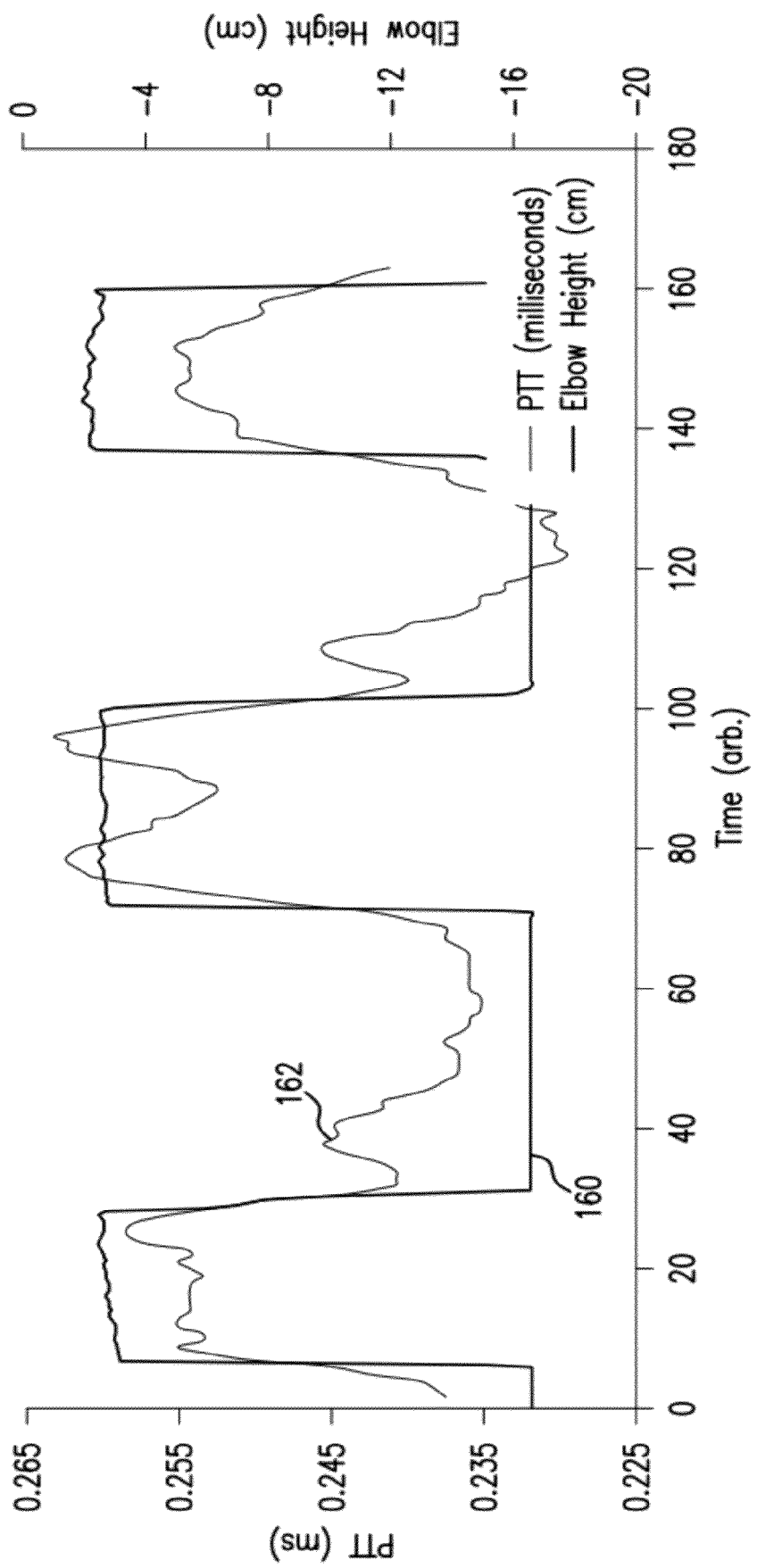
FIG. 10 is a graph of time-dependent waveforms indicating a patient's elbow height and corresponding PTT.

FIG. 10 shows actual experimental data that illustrate how PTT changes with arm height. Data for this experiment were collected as the subject periodically raised and lowered their arm using a body-worn vital sign monitor similar to that shown in FIGS. 3A and 3B. Such motion would occur, for example, if the patient was walking. As shown in FIG. 10, changes in the patient's elbow height are represented by time-dependent changes in the DC portion of an ACC waveform, indicated by trace 160. These data are measured directly from an accelerometer positioned near the patient's bicep, as described above. PTT is measured from the same arm using the PPG and ECG waveforms, and is indicated by trace 162. As the patient raises and lowers their arm their PTT rises and falls accordingly, albeit with some delay due to the reaction time of the patient's cardiovascular system.

Calculating a Patient's Posture

Figure 7:
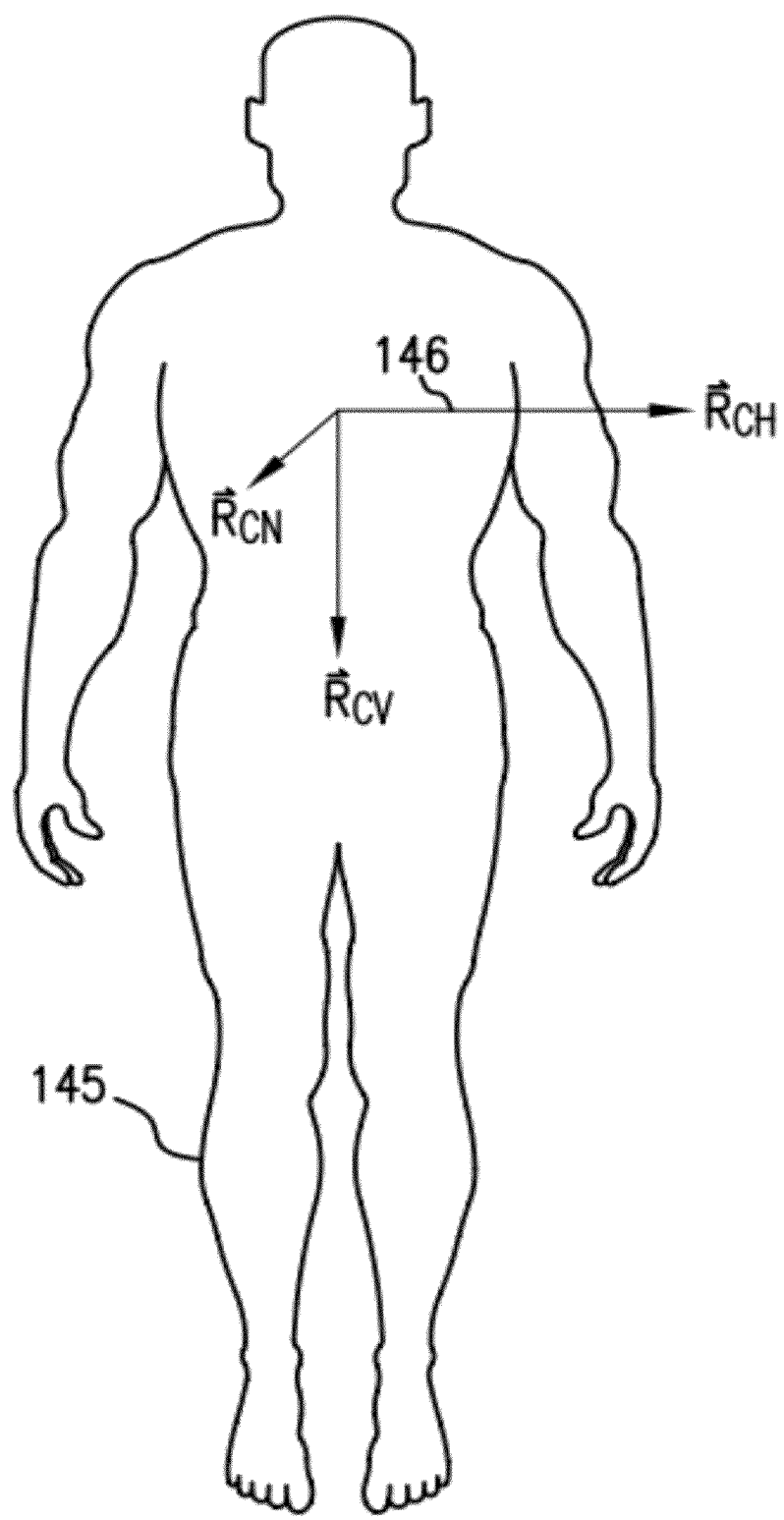
FIG. 7 shows a schematic drawing of a coordinate system representing an accelerometer coordinate space superimposed on a patient's torso.

As described above, a patient's posture can influence how the above-described system generates alarms/alerts. The body-worn monitor can determine a patient's posture using time-dependent ACC waveforms continuously generated from the three patient-worn accelerometers, as shown in FIGS. 3A, B. In embodiments, the accelerometer worn on the patient's chest can be exclusively used to simplify this calculation. An algorithm operating on the wrist-worn transceiver extracts DC values from waveforms measured from this accelerometer and processes them with an algorithm described below to determine posture. Specifically, referring to FIG. 7, torso posture is determined for a patient 145 using angles determined between the measured gravitational vector and the axes of a torso coordinate space 146. The axes of this space 146 are defined in a three-dimensional Euclidean space where $\vec{R}_{CV}$ is the vertical axis, $\vec{R}_{CH}$ is the horizontal axis, and $\vec{R}_{CN}$ is the normal axis. These axes must be identified relative to a 'chest accelerometer coordinate space' before the patient's posture can be determined.

The first step in this procedure is to identify alignment of $\vec{R}_{CV}$ in the chest accelerometer coordinate space. This can be determined in either of two approaches. In the first approach, $\vec{R}_{CV}$ is assumed based on a typical alignment of the body-worn monitor relative to the patient. During manufacturing, these parameters are then preprogrammed into firmware operating on the wrist-worn transceiver. In this procedure it is assumed that accelerometers within the body-worn monitor are applied to each patient with essentially the same configuration. In the second approach, $\vec{R}_{CV}$ is identified on a patient-specific basis. Here, an algorithm operating on the wrist-worn transceiver prompts the patient (using, e.g., video instruction operating on the display, or audio instructions transmitted through the speaker) to assume a known position with respect to gravity (e.g., standing up with arms pointed straight down). The algorithm then calculates $\vec{R}_{CV}$ from DC values corresponding to the x, y, and z axes of the chest accelerometer while the patient is in this position. This case, however, still requires knowledge of which arm (left or right) the monitor is worn on, as the chest accelerometer coordinate space can be rotated by 180 degrees depending on this orientation. A medical professional applying the monitor can enter this information using the GUI, described above. This potential for dual-arm attachment requires a set of two pre-determined vertical and normal vectors which are interchangeable depending on the monitor's location. Instead of manually entering this information, the arm on which the monitor is worn can be easily determined following attachment using measured values from the chest accelerometer values, with the assumption that $\vec{R}_{CV}$ is not orthogonal to the gravity vector.

The second step in the procedure is to identify the alignment of $\vec{R}_{CN}$ in the chest accelerometer coordinate space. The monitor can determine this vector, similar to the way it determines $\vec{R}_{CV}$, with one of two approaches. In the first approach the monitor assumes a typical alignment of the chest-worn accelerometer on the patient. In the second approach, the alignment is identified by prompting the patient to assume a known position with respect to gravity. The monitor then calculates $\vec{R}_{CN}$ from the DC values of the time-dependent ACC waveform.

The third step in the procedure is to identify the alignment of $\vec{R}_{CH}$ in the chest accelerometer coordinate space. This vector is typically determined from the vector cross product of $\vec{R}_{CV}$ and $\vec{R}_{CN}$, or it can be assumed based on the typical alignment of the accelerometer on the patient, as described above.

Figure 8:
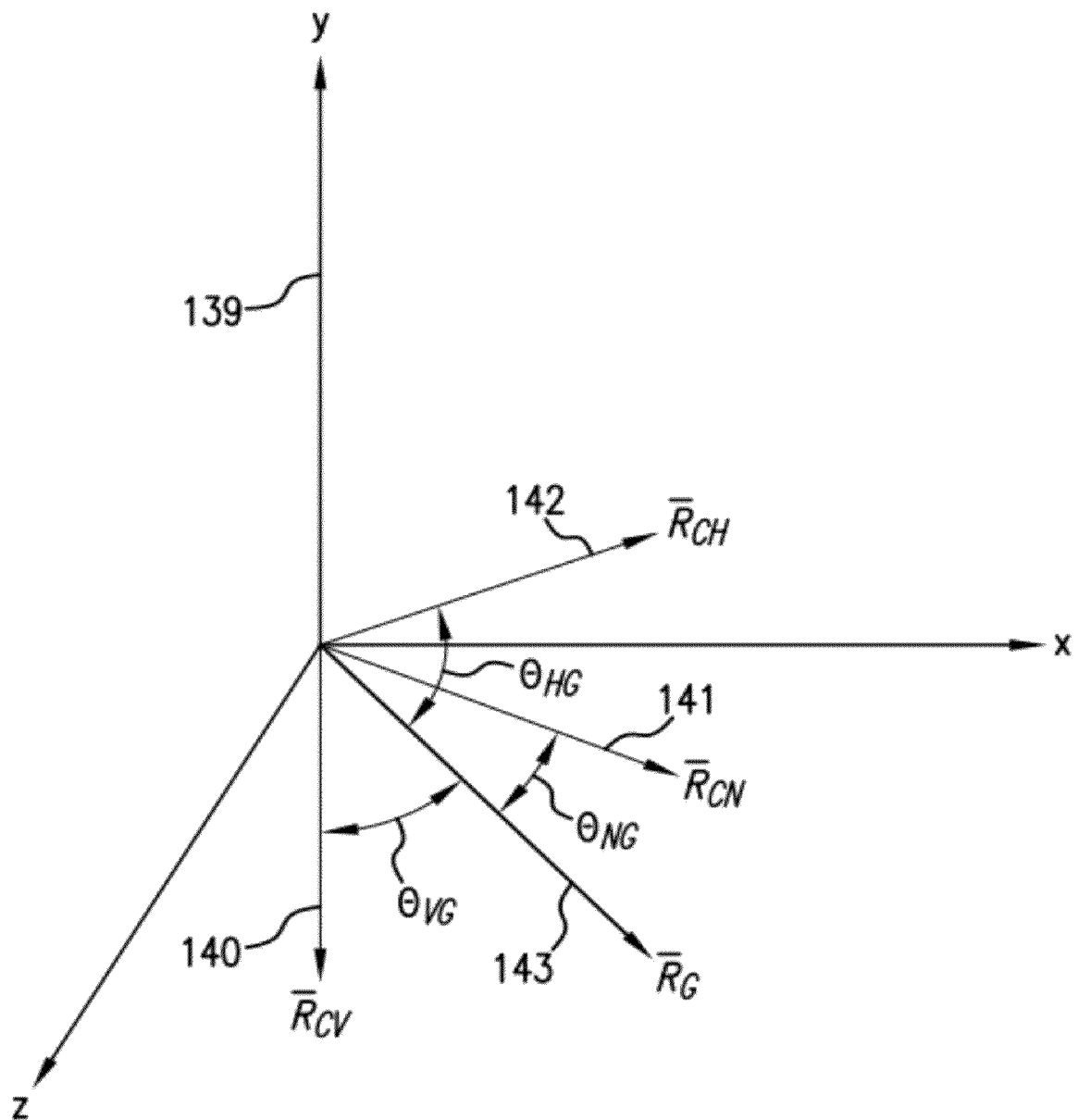
FIG. 8 shows the accelerometer coordinate space of FIG. 7 and a vector representing the direction and magnitude of gravity, along with angles separating the vector from each axis of the coordinate system.

FIG. 8 shows the geometrical relationship between $\vec{R}_{CV}$ 140, $\vec{R}_{CN}$ 141, and $\vec{R}_{CH}$ 142 and a gravitational vector $\vec{R}_G$ 143 measured from a moving patient in a chest accelerometer coordinate space 139. The body-worn monitor continually determines a patient's posture from the angles separating these vectors. Specifically, the monitor continually calculates $\vec{R}_G$ 143 for the patient using DC values from the ACC waveform measured by the chest accelerometer. From this vector, the body-worn monitor identifies angles ($\theta_{VG}$, $\theta_{NG}$, and $\theta_{HG}$) separating it from $\vec{R}_{CV}$ 140, $\vec{R}_{CN}$ 141, and $\vec{R}_{CH}$ 142. The body-worn monitor then compares these three angles to a set of predetermine posture thresholds to classify the patient's posture.

The derivation of this algorithm is as follows. Based on either an assumed orientation or a patient-specific calibration procedure described above, the alignment of $\vec{R}_{CV}$ in the chest accelerometer coordinate space is given by:

$$\vec{R}_{CV} = r_{CVx}\hat{i} + r_{CVy}\hat{j} + r_{CVz}\hat{k} \tag{22}$$

At any given moment, $\vec{R}_G$ is constructed from DC values of the ACC waveform from the chest accelerometer along the x, y, and z axes:

$$\vec{R}_G[n] = y_{Cx}[n]\hat{i} + y_{Cy}[n]\hat{j} + y_{Cz}[n]\hat{k} \tag{23}$$

Equation (24) shows specific components of the ACC waveform used for this calculation:

$$y_{Cx}[n] = y_{DC,chest,x}[n];\ y_{Cy}[n] = y_{DC,chest,y}[n];\ y_{Cz}[n] = y_{DC,chest,z}[n] \tag{24}$$

The angle between $\vec{R}_{CV}$ and $\vec{R}_G$ is given by equation (25):

$$\theta_{VG}[n] = \arccos\left(\frac{\vec{R}_G[n] \cdot \vec{R}_{CV}}{\|\vec{R}_G[n]\| \|\vec{R}_{CV}\|}\right) \tag{25}$$

where the dot product of the two vectors is defined as:

$$\vec{R}_G[n] \cdot \vec{R}_{CV} = (y_{Cx}[n] \times r_{CVx}) + (y_{Cy}[n] \times r_{CVy}) + (y_{Cz}[n] \times r_{CVz}) \tag{26}$$

The definition of the norms of $\vec{R}_G$ and $\vec{R}_{CV}$ are given by equations (27) and (28):

$$\|\vec{R}_G[n]\| = \sqrt{(y_{Cx}[n])^2 + (y_{Cy}[n])^2 + (y_{Cz}[n])^2} \tag{27}$$

$$\|\vec{R}_{CV}\| = \sqrt{(r_{CVx})^2 + (r_{CVy})^2 + (r_{CVz})^2} \tag{28}$$

As shown in equation (29), the monitor compares the vertical angle $\theta_{VG}$ to a threshold angle to determine whether the patient is vertical (i.e. standing upright) or lying down:

$$\text{if } \theta_{VG} \leq 45° \text{ then Torso State}=0, \text{ the patient is upright} \tag{29}$$

If the condition in equation (29) is met the patient is assumed to be upright, and their torso state, which is a numerical value equated to the patient's posture, is equal to 0. The torso state is processed by the body-worn monitor to indicate, e.g., a specific icon corresponding to this state. The patient is assumed to be lying down if the condition in equation (8) is not met, i.e. $\theta_{VG}$>45 degrees. Their lying position is then determined from angles separating the two remaining vectors, as defined below.

The angle $\theta_{NG}$ between $\vec{R}_{CN}$ and $\vec{R}_G$ determines if the patient is lying in the supine position (chest up), prone position (chest down), or on their side. Based on either an assumed orientation or a patient-specific calibration procedure, as described above, the alignment of $\vec{R}_{CN}$ is given by equation (30), where i, j, k represent the unit vectors of the x, y, and z axes of the chest accelerometer coordinate space respectively:

$$\vec{R}_{CN} = r_{CNx}\hat{i} + r_{CNy}\hat{j} + r_{CNz}\hat{k} \tag{30}$$

The angle between $\vec{R}_{CN}$ and $\vec{R}_G$ determined from DC values extracted from the chest accelerometer ACC waveform is given by equation (31):

$$\theta_{NG}[n] = \arccos\left(\frac{\vec{R}_G[n] \cdot \vec{R}_{CN}}{\|\vec{R}_G[n]\| \|\vec{R}_{CN}\|}\right) \tag{31}$$

The body-worn monitor determines the normal angle $\theta_{NG}$ and then compares it to a set of predetermined threshold angles to determine which position the patient is lying in, as shown in equation (32):

$$\text{if } \theta_{NG} \leq 35° \text{ then Torso State}=1, \text{ the patient is supine}$$

$$\text{if } \theta_{NG} \geq 135° \text{ then Torso State}=2, \text{ the patient is prone} \tag{32}$$

If the conditions in equation (32) are not met then the patient is assumed to be lying on their side. Whether they are lying on their right or left side is determined from the angle calculated between the horizontal torso vector and measured gravitational vectors, as described above.

The alignment of $\vec{R}_{CH}$ is determined using either an assumed orientation, or from the vector cross-product of $\vec{R}_{CV}$ and $\vec{R}_{CN}$ as given by equation (33), where i, j, k represent the unit vectors of the x, y, and z axes of the accelerometer coordinate space respectively. Note that the orientation of the calculated vector is dependent on the order of the vectors in the operation. The order below defines the horizontal axis as positive towards the right side of the patient's body.

$$\vec{R}_{CH} = r_{CHx}\hat{i} + r_{CHy}\hat{j} + r_{CHz}\hat{k} = \vec{R}_{CV} \times \vec{R}_{CN} \tag{33}$$

The angle $\theta_{HG}$ between $\vec{R}_{CH}$ and $\vec{R}_G$ is determined using equation (34):

$$\theta_{HG}[n] = \arccos\left(\frac{\vec{R}_G[n] \cdot \vec{R}_{CH}}{\|\vec{R}_G[n]\|\|\vec{R}_{CH}\|}\right) \quad (34)$$

The monitor compares this angle to a set of predetermined threshold angles to determine if the patient is lying on their right or left side, as given by equation (35):

if $\theta_{HG} \geq 90°$ then Torso State=3, the patient is on their right side if $\theta_{NG} < 90°$ then Torso State=4, the patient is on their left side (35)

Table 1 describes each of the above-described postures, along with a corresponding numerical torso state used to render, e.g., a particular icon:

TABLE 1 postures and their corresponding torso states

| Posture | Torso State |
| --- | --- |
| Upright | 0 |
| supine: lying on back | 1 |
| prone: lying on chest | 2 |
| lying on right side | 3 |
| lying on left side | 4 |
| undetermined posture | 5 |

Figure 9A:
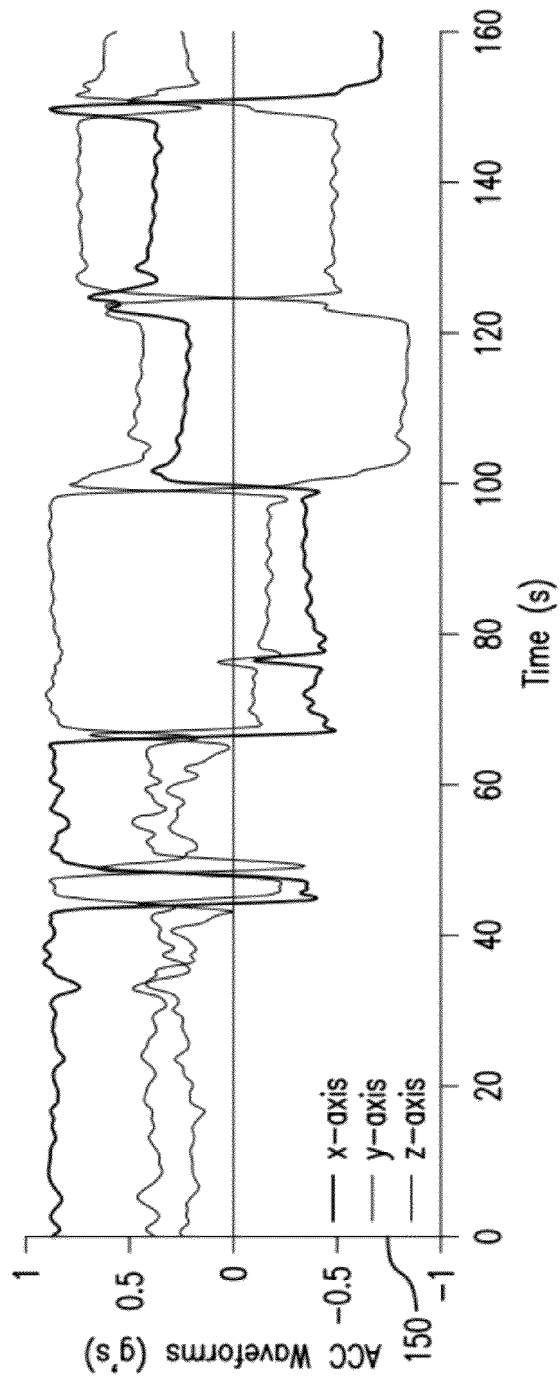
FIG. 9A is a graph showing time-dependent motion waveforms corresponding to different posture states and measured with an accelerometer positioned on a patient's chest.
Figure 9B:
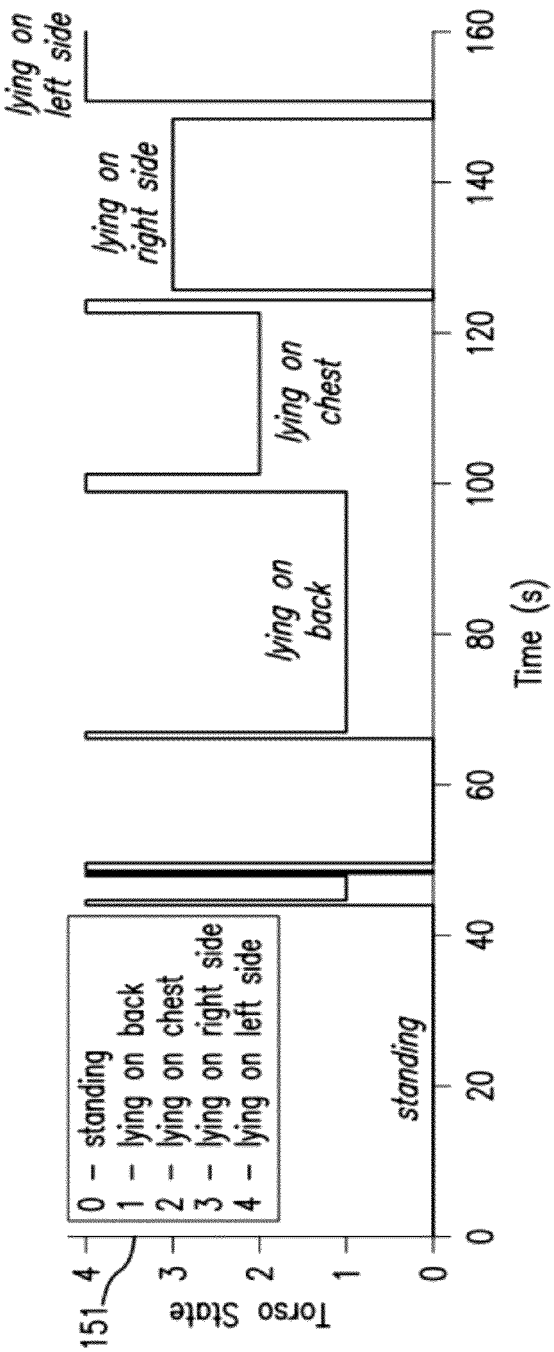
FIG. 9B is a graph showing posture states calculated using the time-dependent motion waveforms of FIG. 9A and a mathematical model for determining a patient's posture.

FIGS. 9A and 9B show, respectively, graphs of time-dependent ACC waveforms 150 measured along the x, y, and z-axes, and the torso states (i.e. postures) 151 determined from these waveforms for a moving patient. As the patient moves, the DC values of the ACC waveforms measured by the chest accelerometer vary accordingly, as shown by the graph 150 in FIG. 9A. The body-worn monitor processes these values as described above to continually determine $\vec{R}_G$ and the various quantized torso states for the patient, as shown in the graph 151 in FIG. 9B. The torso states yield the patient's posture as defined in Table 1. For this study the patient rapidly alternated between standing, lying on their back, chest, right side, and left side within about 150 seconds. As described above, different alarm/alert conditions (e.g. threshold values) for vital signs can be assigned to each of these postures, or the specific posture itself may result in an alarm/alert. Additionally, the time-dependent properties of the graph 151 can be analyzed (e.g. changes in the torso states can be counted) to determine, for example, how often the patient moves in their hospital bed. This number can then be equated to various metrics, such as a 'bed sore index' indicating a patient that is so stationary in their bed that lesions may result. Such a state could then be used to trigger an alarm/alert to the supervising medical professional.

Calculating a Patient's Activity

An algorithm can process information generated by the accelerometers described above to determine a patient's specific activity (e.g., walking, resting, convulsing), which is then used to reduce the occurrence of false alarms. This classification is done using a 'logistic regression model classifier', which is a type of classifier that processes continuous data values and maps them to an output that lies on the interval between 0 and 1. A classification 'threshold' is then set as a fractional value within this interval. If the model output is greater than or equal to this threshold, the classification is declared 'true', and a specific activity state can be assumed for the patient. If the model output falls below the threshold, then the specific activity is assumed not to take place.

This type of classification model offers several advantages. First, it provides the ability to combine multiple input variables into a single model, and map them to a single probability ranging between 0 and 1. Second, the threshold that allows the maximum true positive outcomes and the minimum false positive outcomes can be easily determined from a ROC curve, which in turn can be determined using empirical experimentation and data. Third, this technique requires minimal computation.

The formula for the logistic regression model is given by equation (36) and is used to determine the outcome, P, for a set of buffered data:

$$P = \frac{1}{1 - \exp(-z)} \quad (36)$$

The logit variable z is defined in terms of a series of predictors $(x_i)$, each affected by a specific type of activity, and determined by the three accelerometers worn by the patient, as shown in equation (37):

$$z = b_0 + b_1 x_1 + b_2 x_2 + \ldots + b_m x_m \quad (37)$$

In this model, the regression coefficients $(b_i, i=0, 1, \ldots, m)$ and the threshold $(P_{th})$ used in the patient motion classifier and signal corruption classifiers are determined empirically from data collected on actual subjects. The classifier results in a positive outcome as given in equation (38) if the logistic model output, P, is greater than the predetermined threshold, $P_{th}$:

If $P \geq P_{th}$ then Classifier State=1 (38)

Figure 11A:
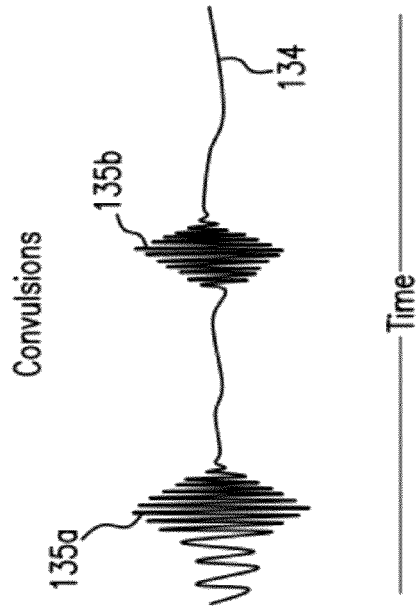
FIGS. 11A and 11C are graphs of time-dependent waveforms generated with an accelerometer that represent, respectively, a patient walking and convulsing.
Figure 11B:
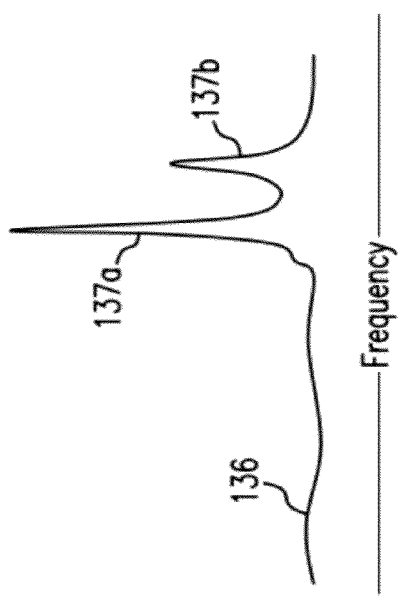
FIGS. 11B and 11D are graphs of frequency-dependent waveforms representing the power spectra of the time-dependent waveforms shown, respectively, in FIGS. 11A and 11C.
Figure 11C:
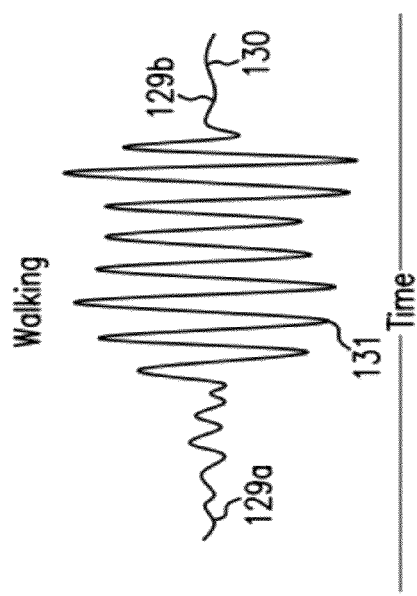
Figure 11D:
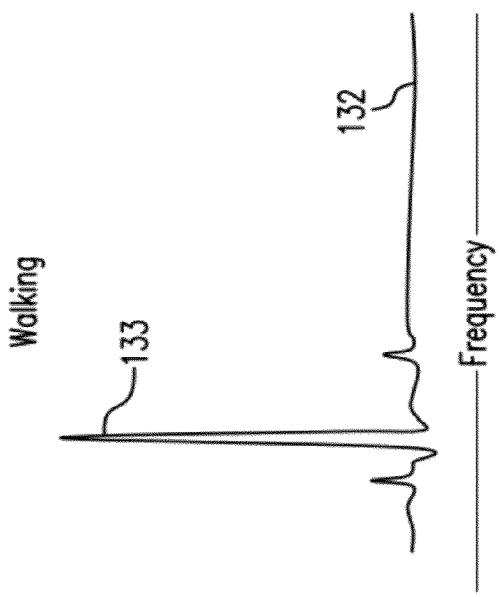

FIGS. 11A-D indicate how the above-described predictors can be processed to determine a patient's specific activity level. As shown in FIG. 11A, a time-dependent ACC waveform 130 measured with an accelerometer from a walking patient typically features DC portions before 129a and after 129b the patient finishes walking, and a periodic AC portion 131 measured during walking. A Fourier Transform of the waveform, as shown by the frequency-dependent waveform 132 in FIG. 11B, yields a power spectrum featuring a well-defined frequency component 133 (typically near 1-3 Hz, with an average of about 1.5 Hz), corresponding to the frequency of the patient's stride. FIGS. 11C and 11D indicate another activity state. Here, the patient is convulsing, and the time-dependent ACC waveform 134 shown in FIG. 11C features two oscillating 'bursts' 135a, 135b separated by periods of inactivity. A Fourier Transform of this waveform, as shown by the power spectrum 136 in FIG. 11D, indicates two frequency components 137a, 137b, both having relatively large values (typically 4-8 Hz, depending on the type of convulsion) compared to that shown in FIG. 11B. These frequency components 137a, 137b correspond to the frequency-dependent content of the oscillating bursts 135a, 135b.

Figure 12:
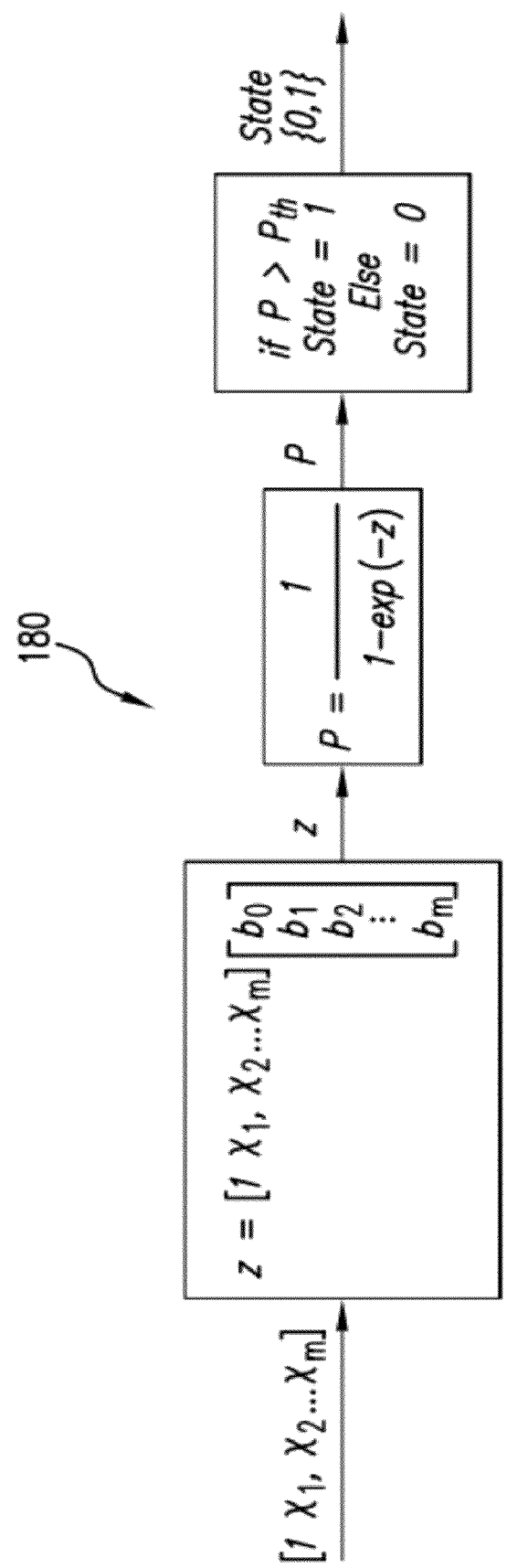
FIG. 12 is a schematic drawing of a calculation used to determine a type of activity state exhibited by a patient.

FIG. 12 shows a block diagram 180 indicating the mathematical model used to determine the above-described logistic regression model classifier. In this model, the series of predictor variables $(x_i)$ are determined from statistical properties of the time-dependent ACC waveforms, along with specific frequency components contained in the power spectra of these waveforms. The frequency components are determined in a low-frequency region (0-20 Hz) of these spectra that corresponds to human motion. Specifically, the predictor variables can be categorized by first taking a power spectrum of a time-dependent ACC waveform generated by an accelerometer, normalizing it, and then separating the fractional power into frequency bands according to Table 2, below:

TABLE 2 predictor variables and their relationship to the accelerometer signal

| predictor variable | Description |
|---|---|
| $x_1$ | normalized power of the AC component of the time-dependent accelerometer signal |
| $x_2$ | average arm angle measured while time-dependent accelerometer signal is collected |
| $x_3$ | standard deviation of the arm angle while time-dependent accelerometer signal is collected |
| $x_4$ | fractional power of the AC component of the frequency-dependent accelerometer signal between 0.5-1.0 Hz |
| $x_5$ | fractional power of the AC component of the frequency-dependent accelerometer signal between 1.0-2.0 Hz |
| $x_6$ | fractional power of the AC component of the frequency-dependent accelerometer signal between 2.0-3.0 Hz |
| $x_7$ | fractional power of the AC component of the frequency-dependent accelerometer signal between 3.0-4.0 Hz |
| $x_8$ | fractional power of the AC component of the frequency-dependent accelerometer signal between 4.0-5.0 Hz |
| $x_9$ | fractional power of the AC component of the frequency-dependent accelerometer signal between 5.0-6.0 Hz |
| $x_{10}$ | fractional power of the AC component of the frequency-dependent accelerometer signal between 6.0-7.0 Hz |

The predictor variables described in Table 2 are typically determined from ACC signals generated by accelerometers deployed in locations that are most affected by patient motion. Such accelerometers are typically mounted directly on the wrist-worn transceiver, and on the bulkhead connector attached to the patient's arm. The normalized signal power ($x_i$) for the AC components ($y_{W,i}$, i=x, y, z) calculated from the ACC is shown in equation (39), where $F_s$ denotes the signal sampling frequency, N is the size of the data buffer, and $x_{norm}$ is a predetermined power value:

$$x_1 = \frac{1}{x_{norm}}\left(\frac{F_S}{N}\right)\sum_{n=1}^{N}[(y_{W,x}[n])^2 + (y_{W,y}[n])^2 + (y_{W,z}[n])^2] \quad (39)$$

The average arm angle predictor value ($x_2$) was determined using equation (40):

$$x_2 = \left(\frac{1}{N}\right)\sum_{n=1}^{N}\cos(\theta_{GW}[n]) \quad (40)$$

Note that, for this predictor value, it is unnecessary to explicitly determine the angle $_{GW}$ using an arccosine function, and the readily available cosine value calculated in equation (12) acts as a surrogate parameter indicating the mean arm angle.

The predictor value indicating the standard deviation of the arm angle ($x_3$) was determined using equation (41) using the same assumptions for the angle $_{GW}$ as described above:

$$x_3 = \sqrt{\left(\frac{1}{N}\right)\sum_{n=1}^{N}(\cos(\theta_{GW}[n]) - x_2)^2} \quad (41)$$

The remaining predictor variables ($x_4$-$x_{10}$) are determined from the frequency content of the patient's motion, determined from the power spectrum of the time-dependent accelerometer signals, as indicated in FIGS. 11B and 11D. To simplify implementation of this methodology, it is typically only necessary to process a single channel of the ACC waveform. Typically, the single channel that is most affected by patient motion is $y_W$, which represents motion along the long axis of the patient's lower arm, determined from the accelerometer mounted directly in the wrist-worn transceiver. Determining the power requires taking an N-point Fast Fourier Transform (FFT) of the accelerometer data ($X_W[m]$); a sample FFT data point is indicated by equation (42):

$$X_W[m] = a_m + ib_m \quad (42)$$

Once the FFT is determined from the entire time-domain ACC waveform, the fractional power in the designated frequency band is given by equation (43), which is based on Parseval's theorem. The term mStart refers to the FFT coefficient index at the start of the frequency band of interest, and the term mEnd refers to the FFT coefficient index at the end of the frequency band of interest:

$$x_k = \left(\frac{1}{P_T}\right)\sum_{m=mStart}^{mEnd}(a_m + ib_m)(a_m - ib_m) \quad (43)$$

Finally, the formula for the total signal power, $P_T$, is given in equation (44):

$$P_T = \sum_{m=0}^{N/2}(a_m + ib_m)(a_m - ib_m) \quad (44)$$

As described above, to accurately estimate a patient's activity level, predictor values $x_1$-$x_{10}$ defined above are measured from a variety of subjects selected from a range of demographic criteria (e.g., age, gender, height, weight), and then processed using predetermined regression coefficients ($b_j$) to calculate a logit variable (defined in equation (37)) and the corresponding probability outcome (defined in equation (36)). A threshold value is then determined empirically from an ROC curve. The classification is declared true if the model output is greater than or equal to the threshold value. During an actual measurement, an accelerometer signal is measured and then processed as described above to determine the predictor values. These parameters are used to determine the logit and corresponding probability, which is then compared to a threshold value to estimate the patient's activity level.

Figure 13A:
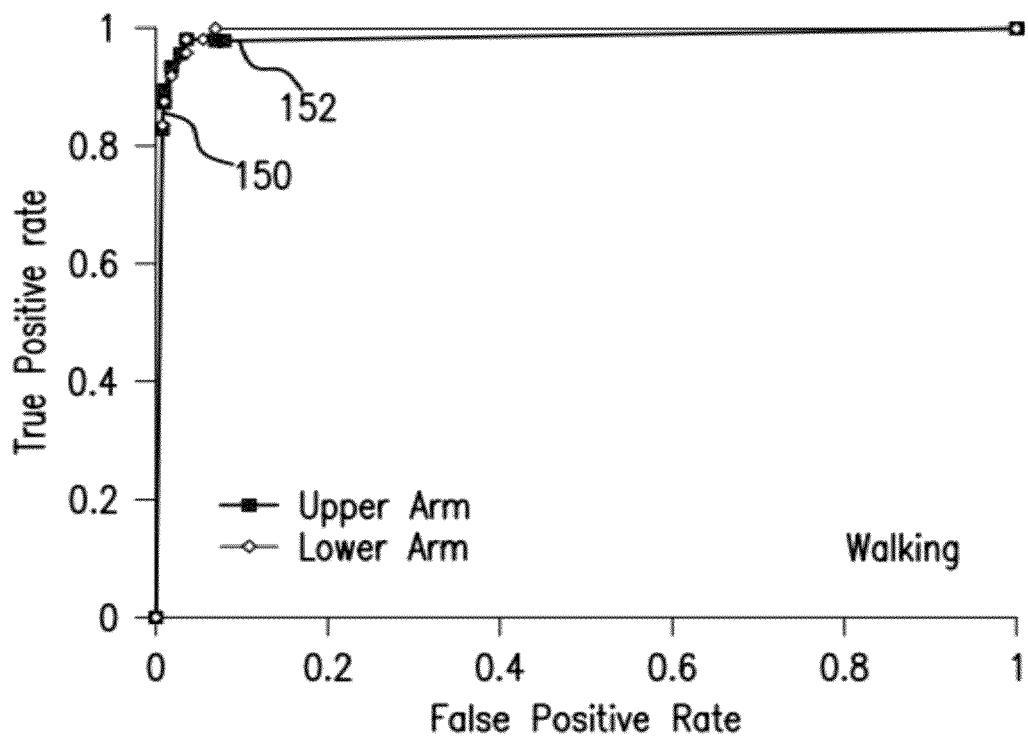
FIGS. 13A and 13B are receiver operating characteristic (ROC) curves that show results from the calculation of FIG. 12 for, respectively, a patient that is walking and resting.

FIGS. 13A,B show actual ROC curves, determined using accelerometers placed on the upper and lower arms of a collection of patients. An ideal ROC curve indicates a high true positive rate (shown on the y-axis) and a low false positive rate (shown on the x-axis), and thus has a shape closely representing a 90 degree angle. From such a curve a relatively high threshold can be easily determined and used as described above to determine a patient's activity level. Ultimately this results in a measurement that yields a high percentage of 'true positives', and a low percentage of 'false positives'. FIG. 13A shows, for example, a ROC curve generated from the patients' upper 192 and lower 190 arms during walking. Data points on the curves 190, 192 were generated with accelerometers and processed with algorithms as described above. The distribution of these data indicates that this approach yields a high selectivity for determining whether or not a patient is walking.

Figure 13B:
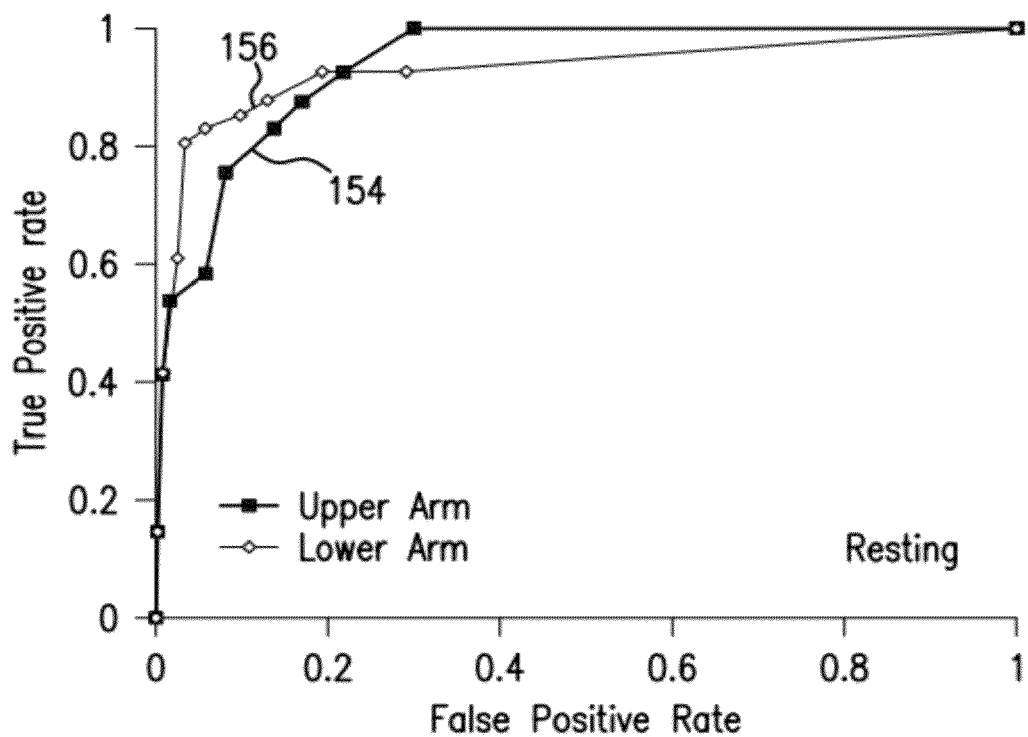

FIG. 13B shows data measured during resting. The ACC waveforms measured for this activity state feature fewer well-defined frequency components compared to those measured for FIG. 13A, mostly because the act of 'resting' is not as well defined as that of 'walking'. That is why the ROC curves measured from the upper 194 and lower 196 arms have less of an idealized shape. Still, from these data threshold values can be determined that can be used for future measurements to accurately characterize whether or not the patient is resting.

ROC curves similar to those shown in FIGS. 13A,B can be generated empirically from a set of patients undergoing a variety of different activity states. These states include, among others, falling, convulsing, running, eating, and undergoing a bowel movement. A threshold value for each activity state is determined once the ROC curve is generated, and going forward this information can be incorporated in an algorithm for estimating the patient's activity. Such an algorithm, e.g., can be uploaded wirelessly to the wrist-worn transceiver.

Figure 14:
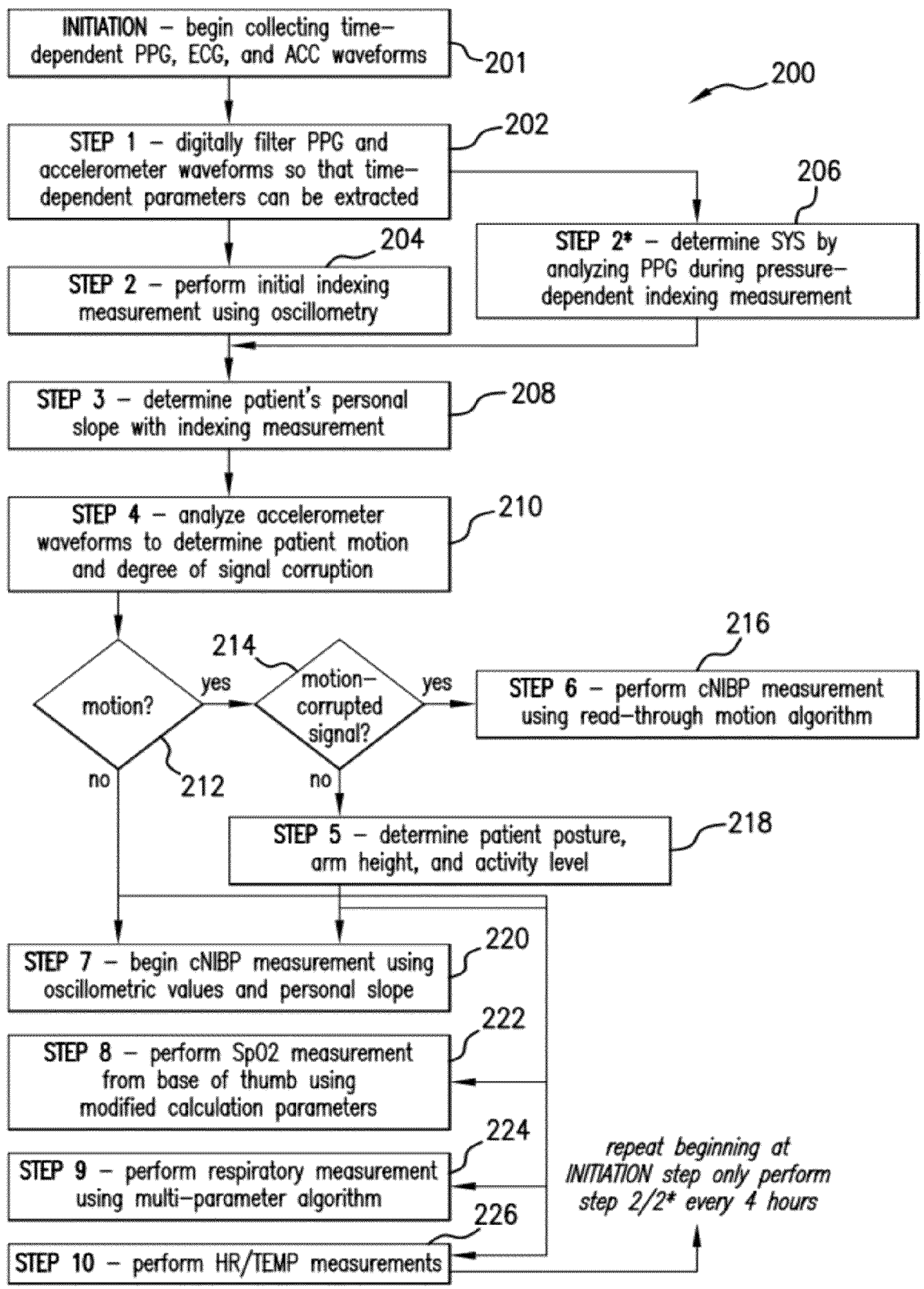
FIG. 14 is a flow chart describing an algorithm that processes information from the body-worn vital sign monitor of FIGS. 3A, 3B, and 4 to continuously determine a patient's vital signs and motion.

FIG. 14 is a flow chart 200 showing the various algorithms described above, along with other supporting algorithms described in co-pending patent application, the contents of which are fully incorporated herein by reference.

The initiation phase of the algorithm begins with collection of time-dependent PPG, ECG, ACC, and pressure waveforms using analog and digital circuitry within the body-worn vital sign monitor described above (step 201). An optical sensor attached to the patient's thumb measures PPG waveforms, while an ECG circuit attached to three electrodes on the patient's chest measures ECG waveforms. Once collected, these waveforms are digitally filtered according to step 202 using standard frequency-domain techniques to remove any out-of-band noise. The pressure waveform, generated during an indexing measurement during step 204 using a pneumatic system and cuff wrapped around the patient's bicep, is measured during inflation and processed using oscillometry, as described in the above-referenced patent application entitled: 'VITAL SIGN MONITOR FOR MEASURING BLOOD PRESSURE USING OPTICAL, ELECTRICAL, AND PRESSURE WAVEFORMS' (U.S. Ser. No. 12/138, 194; filed Jun. 12, 2008), the contents of which have been previously incorporated herein by reference. This yields an indirect measurement of SYS, DIA, and MAP values. Alternatively, SYS can be determined directly by processing the PPG in the presence of applied pressure according to step 206 (as described in patent application referenced immediately above). PTT is measured as a function of applied pressure during the indexing measurement, and is processed during step 208 according to determine a personal, patient-specific slope (as described in patent application referenced immediately above). This slope, along with blood pressure values determined with oscillometry during the indexing measurement, is used along with PTT values measured from a temporal separation between the ECG and PPG to determine cNIBP according to step 220 (as described in patent application referenced immediately above).

Motion, as described in detail above, can complicate measurement of the above-described parameters, and is determined by processing time-dependent ACC signals from multiple accelerometers attached to the patient and connected to the body-worn vital sign monitor. These signals are processed according to steps 210, 212, and 214, as described in detail above, to determine the degree of motion-based signal corruption, and according to step 218 to determine posture, arm height, and activity level. If motion is determined to be present, cNIBP can be estimated according to step 216 using a read-through technique.

SpO2 is measured according to step 222 with the body-worn vital sign monitor using an integrated reference hardware design, algorithm, and code base provided by OSI of Hawthorne, Calif. Conventional algorithms for SpO2 are optimized for measurements made at the tip of the patient's index finger. However, since optical measurements with the body-worn vital sign monitor described above are typically made from the base of the patient's thumb, a modified set of calibration parameters need to be experimentally determined for this location using informal clinical trials.

The above-described measurements for PTT-based cNIBP are performed according to step 220 by collecting data for 20-second periods, and then processing these data with a variety of statistical averaging techniques. Pressure-dependent indexing measurements according to steps 204 and 206 are performed every 4 hours. In the algorithm described above, a technique for rolling averages can be deployed, allowing values for cNIBP (step 220), HR and TEMP (step 226), RR (step 224), and SpO2 (step 222) to be displayed every second. The interval for pressure-dependent indexing measurements may be extended past four hours.

In addition to those methods described above, a number of additional methods can be used to calculate blood pressure from the optical and electrical waveforms. These are described in the following co-pending patent applications, the contents of which are incorporated herein by reference: 1) CUFFLESS BLOOD-PRESSURE MONITOR AND ACCOMPANYING WIRELESS, INTERNET-BASED SYSTEM (U.S. Ser. No. 10/709,015; filed Apr. 7, 2004); 2) CUFFLESS SYSTEM FOR MEASURING BLOOD PRESSURE (U.S. Ser. No. 10/709,014; filed Apr. 7, 2004); 3) CUFFLESS BLOOD PRESSURE MONITOR AND ACCOMPANYING WEB SERVICES INTERFACE (U.S. Ser. No. 10/810,237; filed Mar. 26, 2004); 5) CUFFLESS BLOOD PRESSURE MONITOR AND ACCOMPANYING WIRELESS MOBILE DEVICE (U.S. Ser. No. 10/967,511; filed Oct. 18, 2004); 6) BLOOD PRESSURE MONITORING DEVICE FEATURING A CALIBRATION-BASED ANALYSIS (U.S. Ser. No. 10/967,610; filed Oct. 18, 2004); 7) PERSONAL COMPUTER-BASED VITAL SIGN MONITOR (U.S. Ser. No. 10/906,342; filed Feb. 15, 2005); 8) PATCH SENSOR FOR MEASURING BLOOD PRESSURE WITHOUT A CUFF (U.S. Ser. No. 10/906,315; filed Feb. 14, 2005); 9) PATCH SENSOR FOR MEASURING VITAL SIGNS (U.S. Ser. No. 11/160,957; filed Jul. 18, 2005); 10) WIRELESS, INTERNET-BASED SYSTEM FOR MEASURING VITAL SIGNS FROM A PLURALITY OF PATIENTS IN A HOSPITAL OR MEDICAL CLINIC (U.S. Ser. No. 11/162,719; filed Sep. 9, 2005); 11) HAND-HELD MONITOR FOR MEASURING VITAL SIGNS (U.S. Ser. No. 11/162,742; filed Sep. 21, 2005); 12) CHEST STRAP FOR MEASURING VITAL SIGNS (U.S. Ser. No. 11/306, 243; filed Dec. 20, 2005); 13) SYSTEM FOR MEASURING VITAL SIGNS USING AN OPTICAL MODULE FEATURING A GREEN LIGHT SOURCE (U.S. Ser. No. 11/307,375; filed Feb. 3, 2006); 14) BILATERAL DEVICE, SYSTEM AND METHOD FOR MONITORING VITAL SIGNS (U.S. Ser. No. 11/420,281; filed May 25, 2006); 15) SYSTEM FOR MEASURING VITAL SIGNS USING BILATERAL PULSE TRANSIT TIME (U.S. Ser. No. 11/420,652; filed May 26, 2006); 16) BLOOD PRESSURE MONITOR (U.S. Ser. No. 11/530,076; filed Sep. 8, 2006); 17) TWO-PART PATCH SENSOR FOR MONITORING VITAL SIGNS (U.S. Ser. No. 11/558,538; filed Nov. 10, 2006); and, 18) MONITOR FOR MEASURING VITAL SIGNS AND RENDERING VIDEO IMAGES (U.S. Ser. No. 11/682,177; filed Mar. 5, 2007).

Other embodiments are also within the scope of the invention. For example, other techniques, such as conventional oscillometry measured during deflation, can be used to determine SYS for the above-described algorithms. In another embodiment, 'vascular transit time' (VTT) measured from two PPG waveforms can be used in place of PTT, as described above.

Still other embodiments are within the scope of the following claims.

What is claimed is:

1. A method for monitoring vital signs and posture of a patient, the method comprising the following steps: (a) detecting a first time-dependent physiological waveform indicative of one or more contractile properties of the patient's heart with a first sensor comprising a first detector configured to be worn on the patient's body; (b) detecting a second time-dependent physiological waveform indicative of one or more contractile properties of the patient's heart with a second sensor comprising a second detector configured to be worn on the patient's body; (c) detecting a set of time-dependent motion waveforms with at least one motion-detecting sensor positioned on the patient's torso, wherein the one motion-detecting sensor detects a set of motion waveforms indicative of motion of the patient's torso; (d) processing the first and second time-dependent physiological waveforms to determine at least one vital sign from the patient; (e) analyzing at least a portion of the set of time-dependent motion waveforms, or a mathematical derivative thereof, to determine a vector corresponding to motion of the patient's torso; (f) comparing the vector to a coordinate space representative of how the motion-detecting sensor is oriented on the patient to determine a posture parameter; and (g) comparing the posture parameter to a threshold value to estimate the patient's posture.

2. The method of claim 1, wherein step (e) further comprises analyzing three time-dependent motion waveforms, each corresponding to a unique axis, to determine the vector.

3. The method of claim 2, wherein step (f) further comprises comparing the vector to a coordinate space defined by three positional vectors, each indicating an orientation of the motion-detecting sensor on the patient.

4. The method of claim 3, wherein a first positional vector corresponds to a vertical axis in the coordinate space, a second positional vector corresponds to a horizontal axis in the coordinate space, and the third positional vector corresponds to a normal axis extending normal to the patient's chest.

5. The method of claim 3, wherein the posture parameter is an angle.

6. The method of claim 5, wherein step (f) further comprises comparing the vector to the coordinate space to determine the angle between the vector and at least one of the three positional vectors.

7. The method of claim 6, wherein step (f) further comprises comparing the vector to the coordinate space to determine the angle between the vector and a vector corresponding to a vertical axis, or a property of the angle between the vector and the vector corresponding to the vertical axis.

8. The method of claim 7, wherein step (g) further comprises comparing the angle to a threshold value that is substantially equivalent to 45 degrees, and wherein the patient's posture is estimated to be upright if the angle is less than the threshold value.

9. The method of claim 7, wherein step (g) further comprises comparing the angle to a threshold value that is substantially equivalent to 45 degrees, and wherein the patient's posture is estimated to be lying down if the angle is greater than the threshold value.

10. The method of claim 9, wherein step (f) further comprises comparing the vector to the coordinate space to determine the angle between the vector and a vector corresponding to a normal axis extending normal to the patient's chest, or a property of the angle between the vector and the vector corresponding to a normal axis extending normal to the patient's chest.

11. The method of claim 10, wherein step (g) further comprises comparing the angle to a threshold value that is substantially equivalent to 35 degrees, and wherein the patient's posture is estimated to be supine if the angle is less than the threshold value.

12. The method of claim 10, wherein step (g) further comprises comparing the angle to a threshold value that is substantially equivalent to 135 degrees, and wherein the patient's posture is estimated to be prone if the angle is greater than the threshold value.

13. The method of claim 9, wherein step (f) further comprises comparing the vector to the coordinate space to determine the angle between the vector and a vector corresponding to a horizontal axis, or a property of the angle between the vector and the vector corresponding to the horizontal axis.

14. The method of claim 13, wherein step (g) further comprises comparing the angle to a threshold value that is substantially equivalent to 90 degrees, and wherein the patient's posture is estimated to be lying on a first side if the angle is less than the threshold value.

15. The method of claim 13, wherein step (g) further comprises comparing the angle to a threshold value that is substantially equivalent to 90 degrees, and wherein the patient's posture is estimated to be lying on a side opposite the first side if the angle is greater than the threshold value.

16. The method of claim 1, wherein step (c) further comprises detecting a set of time-dependent motion waveforms with at least one motion-detecting sensor positioned on the patient's chest.

17. The method of claim 1, where the at least one motion-detecting sensor is an accelerometer.

18. The method of claim 1, wherein step (d) further comprises processing the first and second time-dependent physiological waveforms to calculate a time difference between a feature in the first time-dependent physiological waveform and a feature in the second time-dependent physiological waveform.

19. The method of claim 18, wherein step (d) further comprises calculating a blood pressure from the time difference.

20. The method of claim 18, wherein the first time-dependent physiological waveform is an electrical waveform, and step (a) further comprises detecting the electrical waveform with at least two electrodes attached to the patient and operably connected to an electrical circuit.

21. The method of claim 20, wherein the second time-dependent physiological waveform is an optical waveform, and step (b) further comprises detecting the optical waveform with an optical sensor comprising a light source and a photodiode.

22. The method of claim 18, wherein each of the first and second time-dependent physiological waveforms are selected from a group consisting of an optical waveform, an electrical waveform, an acoustic waveform, and a pressure waveform.

23. The method of claim 22, wherein and steps (a) and (b) each further comprise detecting a time-dependent physiological waveform with a sensor selected from a group consisting of: (i) an optical sensor comprising a light source and a photodiode; (ii) an electrical sensor comprising at least two electrodes operably connected to an electrical circuit; (iii) an acoustic sensor comprising a microphone; and (iv) a pressure sensor comprising a transducer.

24. A system for measuring vital signs from a patient, comprising: (a) a first sensor configured to generate a first time-dependent waveform indicative of one or more contractile properties of the patient's heart; (b) a second sensor configured to generate a second time-dependent waveform indicative of one or more contractile properties of the patient's heart; (c) at least three motion-detecting sensors positioned on the forearm, upper arm, and a body location other than the forearm or upper arm of the patient, each of said motion-detecting sensors generating at least one time-dependent motion waveform indicative of motion of the location on the patient's body to which the motion-detecting sensor is affixed; (d) a processing component configured to be worn on the patient's body and comprising a microprocessor, said processing component configured to receive the first time-dependent waveform, the second time-dependent waveform, and the at least one time-dependent motion waveform generated by each motion-detecting sensor and determine therefrom: (i) a pulse transit time calculated using a time difference between a time-dependent feature in each of the first and second time-dependent waveforms, (ii) a blood pressure value calculated using said time difference, and (iii) at least one motion parameter selected from the patient's posture, activity level, and degree of motion calculated using at least one motion waveform generated by each of said motion-detecting sensors; and (e) a wireless communication system configured to be worn on the patient's body and operably connect to the processing component, the wireless system configured to wirelessly transmit the blood pressure value and at least one motion parameter determined by the processing component to a remote receiver.

25. A system for measuring vital signs from a patient, comprising: (a) a sensor configured to detect a first time-dependent physiological waveform indicative of one or more contractile properties of the patient's heart; (b) a cable system comprising: an electrical sensor comprising: at least two electrodes configured to detect electrical signals from the patient's body and operably connect to an electrical circuit configured to process the detected electrical signals, the electrical sensor generating a time-dependent electrical waveform indicative of one or more contractile properties of the patient's heart, and, at least two motion-detecting sensors, each of said motion-detecting sensors generating at least one time-dependent motion waveform indicative of motion of the location on the patient's body to which the motion-detecting sensor is affixed; and, (c) a processing component configured to be worn on the patient's body and comprising a microprocessor and one or more electrical connectors for operably connecting the microprocessor to the sensor and the cable system, said processing component configured to receive the time-dependent electrical waveform, the time-dependent physiological waveform, and the at least one time-dependent motion waveform generated by each motion-detecting sensor and determine therefrom: (i) at least one vital sign calculated using at least one of the time-dependent physiological waveform and the time-dependent electrical waveform, and (ii) at least one motion parameter selected from the patient's posture, activity level, arm height, and degree of motion calculated using at least one time-dependent motion waveform generated by each of said motion-detecting sensors.

26. A method for monitoring a patient, comprising the following steps: (a) detecting a first time-dependent physiological waveform indicative of one or more contractile properties of the patient's heart with a first sensor comprising a first detector configured to be worn on the patient's body; (b) detecting a second time-dependent physiological waveform indicative of one or more contractile properties of the patient's heart with a second sensor comprising a second detector configured to be worn on the patient's body; (c) detecting sets of time-dependent motion waveforms with at least two motion-detecting sensors positioned on different locations on the patient's body, wherein each motion-detecting sensor detects a set of motion waveforms indicative of motion of the location on the patient's body to which the motion-detecting sensor is affixed; (d) processing the first and second time-dependent physiological waveforms to determine at least one vital sign from the patient; (e) analyzing at least a portion of each set of time-dependent motion waveforms, or a mathematical derivative thereof, to determine a motion parameter; (f) processing the motion parameter to determine a probability that the patient is undergoing a specific activity state; and (g) estimating the patient's activity state based on the probability.

27. A system for measuring vital signs from a patient, comprising: (a) a first sensor configured to generate a first time-dependent waveform indicative of one or more contractile properties of the patient's heart; (b) a second sensor configured to generate a second time-dependent waveform indicative of one or more contractile properties of the patient's heart; (c) at least two motion-detecting sensors positioned on a location selected from a forearm, upper arm, and a body location other than the forearm or upper arm of the patient, each of said motion-detecting sensors generating at least one time-dependent motion waveform indicative of motion of the location on the patient's body to which the motion-detecting sensor is affixed; and, (d) a processing component configured to be worn on the patient's body and comprising a microprocessor, said processing component configured to receive the first time-dependent waveform, the second time-dependent waveform, and the at least one time-dependent motion waveform generated by each motion-detecting sensor and determine therefrom: (i) one or more vital signs calculated using the first and second time-dependent waveforms; (ii) at least one motion parameter selected from the patient's posture, activity level, arm height, and degree of motion and calculated using at least one motion waveform generated by each of said motion-detecting sensors; and (iii) at least one alarm condition calculated using one or more of the vital signs and at least one motion parameter, wherein an alarm condition indicated by a variance in one or more of the vital signs is regulated according to one or more motion parameters.

* * * * *